United States Patent
Murphy et al.

(10) Patent No.: US 10,093,807 B2
(45) Date of Patent: Oct. 9, 2018

(54) STABLE YELLOW IMIDAZOLIUM COMPOUNDS

(71) Applicant: NOXELL COPRORATION, Hunt Valley, MD (US)

(72) Inventors: Bryan Patrick Murphy, Loveland, OH (US); Guiru Zhang, Lebanon, OH (US); Garry Steven Garrett, West Chester, OH (US)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 15/267,535

(22) Filed: Sep. 16, 2016

(65) Prior Publication Data

US 2018/0079907 A1   Mar. 22, 2018

(51) Int. Cl.
*C07D 403/12* (2006.01)
*C09B 44/16* (2006.01)
*C07D 487/04* (2006.01)

(52) U.S. Cl.
CPC ............ *C09B 44/16* (2013.01); *C07D 403/12* (2013.01); *C07D 487/04* (2013.01)

(58) Field of Classification Search
CPC ..................................................... C09B 44/16
See application file for complete search history.

(56) References Cited

U.S. PATENT DOCUMENTS

| 4,097,475 | A | 6/1978 | James |
| 6,214,813 | B1 * | 4/2001 | Zhang ................. A61K 31/415 |
| | | | 514/150 |
| 8,034,124 | B2 | 10/2011 | Fadli et al. |
| 8,158,317 | B2 * | 4/2012 | Fujie ..................... B41M 5/388 |
| | | | 106/31.5 |
| 2008/0081269 | A1 | 4/2008 | Fujie et al. |

FOREIGN PATENT DOCUMENTS

| FR | 2266729 A1 | 10/1975 |
| FR | 2917736 A1 | 12/2008 |
| WO | WO-03/032937 A1 | 4/2003 |

OTHER PUBLICATIONS

"International Application Serial No. PCT/US2017/051401, International Search Report dated Dec. 6, 2017", 5 pgs.
"International Application Serial No. PCT/US2017/051401, Written Opinion dated Dec. 6, 2017", 7 pgs.

* cited by examiner

*Primary Examiner* — Paul V Ward
(74) *Attorney, Agent, or Firm* — Schwegman Lundberg & Woessner, P.A.

(57) ABSTRACT

Described herein is a yellow imidazolium chromophore having a structure according to Formula V.

20 Claims, No Drawings

STABLE YELLOW IMIDAZOLIUM COMPOUNDS

TECHNICAL FIELD OF THE INVENTION

Described herein is a class of yellow imidazolium azo compounds that have a simplified chromophore and high relative solubility in aqueous systems, and that are surprisingly stable under in-use conditions. These are useful for dyeing fibers such as hair, wool, and keratinaceous materials. Also described herein are hair color compositions comprising the imidazolium azo compounds that may serve as hair dyes, and methods of using the same. These materials can be used with or without oxidant.

BACKGROUND OF THE INVENTION

In dye chemistry, use of heterocyclic components in the chromophore leads to pure, intense colors. Pure, intense yellows are particularly important in hair dyeing, because they are necessary to deliver attractive gold and warm shades that are rich and brilliant rather than muted, as when less pure colors are used. They not only are needed for adding brightness, but they also can be used to give the appearance of lightening. For yellow direct dyes, one of the challenges is that some of the heterocyclic moieties in dyes, such as thiazolium and pyridinium, can be unstable under in-use conditions. Described herein are yellow imidazolium chromophore compounds that address such challenges.

SUMMARY OF THE INVENTION

Described herein is a compound having a structure according to Formula V

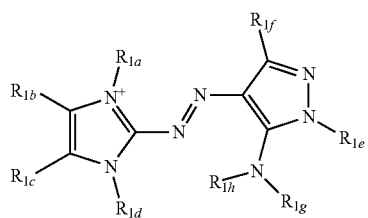

Formula (V)

wherein
(i) $R_{1b}$, $R_{1c}$ and $R_{1f}$ are independently selected from the group consisting of hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or attached to a polymer backbone through a linker group;
(ii) $R_{1a}$, $R_{1d}$, and $R_{1h}$ are independently selected from the group consisting of hydrogen, alkyl, halogen substituted alkyl, alkenyl, alkynyl, aryl, hydroxyalkyl, aminoalkyl, alkyl group carrying a quaternary ammonium cation, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or attached to a polymer backbone through a linker group; and
(iii) $R_{1c}$ and $R_{1g}$ are selected from the group consisting of hydrogen, alkyl, halogen substituted alkyl, alkenyl, alkynyl, aryl, hydroxyalkyl, aminoalkyl, alkyl group carrying a quaternary ammonium cation, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or are attached to a polymer backbone through a linker group, or part of a cyclic structure and joined by substituted or unsubstituted alkyl or heteroalkyl groups.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. When more than one composition is used during a treatment, as in mixing of the components of a typical oxidative dye product, the total weight to be considered is the total weight of all the compositions applied on the hair simultaneously (i.e. the weight found "on head") unless otherwise specified. The term "weight percent" may be denoted as "wt. %" herein.

As used herein, the term "hair" to be treated may be "living" i.e. on a living body or may be "non-living" i.e. in a wig, hairpiece or other aggregation of non-living keratinous fibers. Mammalian, particularly human, hair is preferred. However, wool, fur, and other keratin containing fibers are suitable substrates for the compositions according to the present invention.

As used herein, the term "chromophore" means the part of the direct dye compound responsible for its color.

As used herein, the term "direct dye compound" means a dye used in a process in which dye molecules are attracted by physical forces at the molecular level to a textile or substrate such as the hair. As opposed to oxidative dyes, there is no chemical reaction required to form the chromophore. Additionally, there is no covalent bond formation between the direct dye and the substrate as opposed to reactive dyes. The direct dye compound does not undergo a chemical transformation before and after the dyeing process.

As used herein, the term "core structure" means the chromophore including one or two permanent cations that are pendant to the chromophore or part of the chromophore. In an embodiment, the chromophore is charged. In an embodiment, the chromophore is not charged as the permanent cation is pendant to the chromophore.

As used herein, the term "pendant" means when a functional group is linked to a core structure via covalent bond.

As used herein, the terms "in-use stability" means less than about 6% loss recorded at 30 minutes in the presence of a 3% $H_2O_2$ solution at pH10.6.

The hair colorant compounds described herein comprise one or more washfast direct dyes, optionally, oxidative dyes as well. In an embodiment the hair colorant compositions exhibit in-use stability and/or storage stability.

With regards to the direct dye compounds described herein, numerous tautomeric compounds may be involved. Thus, for example, 2-mercaptopyridine (I) may exist under known conditions in the pyridine-2-thione tautomer form (II).

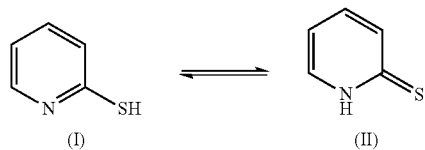

It is to be understood that when this development refers to a particular structure, all of the reasonable additional tautomeric structures are included. In the art, tautomeric structures are frequently represented by one single structure and the method described herein follows this general practice.

It is also understood that within the scope of this invention, E, Z isomers may be involved. Thus, for example, (E)-diphenyldiazene (III) converts under known conditions to (Z)-diphenyldiazene (IV), which is also reversible.

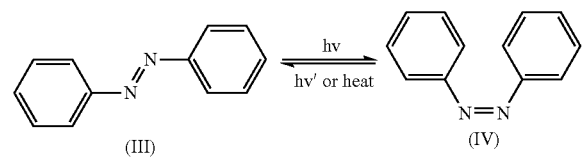

It is to be understood that when this development refers to a particular structure, all of the reasonable additional E, Z isomers are included.

When a salt of Formula (V), described below, contains a cationic moiety, anionic counterions include, for example, D,L-malate, L-malate, D-malate, chloride, bromide, citrate, acetate, lactate, succinate, tartrate, phosphate, hemisulfate, sulfate, methylsulfate, trifluoroacetate, iodide, and mixtures thereof. When a salt of Formula (V) contains an anionic moiety, cationic counterions include, for example, ammonium, substituted ammonium salts (e.g., monoethanolammonium, diethanolammonium, triethanolammonium), sodium, potassium, and mixtures thereof.

I. Yellow Imidazolium Chromophore

Described herein are unique yellow imidazolium chromophores that are storage stable and stable under conditions of use for (1) dyeing of keratinaceous materials, (2) hair dyeing, and (3) fabric dyeing and hueing.

In some embodiments, the compound is of Formula V, or a tautomer or salt thereof

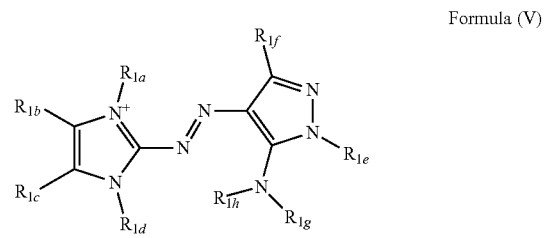

wherein (i) $R_{1b}$, $R_{1c}$ and $R_{1f}$ are each independently hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or are attached to a polymer backbone through a linker;

(ii) $R_{1a}$, $R_{1d}$, and $R_{1h}$ are each independently hydrogen, alkyl, halogen substituted alkyl, alkenyl, alkynyl, aryl, hydroxyalkyl, aminoalkyl, alkyl group carrying a quaternary ammonium cation, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or are attached to a polymer backbone through a linker;

(iii) $R_{1e}$ and $R_{1g}$ are each independently hydrogen, alkyl, halogen substituted alkyl, alkenyl, alkynyl, aryl, hydroxyalkyl, aminoalkyl, alkyl group carrying a quaternary ammonium cation, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or are attached to a polymer backbone through a linker, or part of a cyclic structure and joined by substituted or unsubstituted alkyl or heteroalkyl groups.

In embodiments where the compound of Formula (V) is linked to a polymer, the polymer may be selected from any of a variety of materials. Represented polymers include, but are not limited to, linear polyethyleneimines; branched polyethyleneimines consisting of primary, secondary and tertiary amine groups; polyallylamine hydrochloride; homopolymers or copolymers derived from acrylic or methacrylic esters or amides; copolymers of polystyrene sulfonate (PSS) and poly(4-styrenesulfonic acid-co-maleic acid); peptides, proteins; and the like.

In some embodiments when the compound of Formula (V) is linked to a polymer, the linking group can be of formula (L)

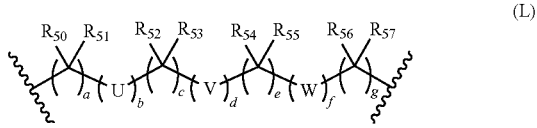

(L)

wherein
(i) L is covalently linked to the compound of Formula (V) either by its left-hand or right-hand side;
(ii) a, c, e and g are each independently an integer from 0 to 3, provided that the sum of a, c, e and g is greater than or equal to 2; b, d and f are each independently 0 or 1; and $R_{50}$, $R_{51}$, $R_{52}$, $R_{53}$, $R_{54}$, $R_{55}$, $R_{56}$ and $R_{57}$ are each independently hydrogen or $C_1$-$C_2$ alkyl group;
(iii) U is an aromatic ring, alkenyl or alkynyl moiety;
(iv) V is O, N or S; and
(v) W is a cyclic aliphatic ring.

II. Hair Color Compositions

In addition to the new yellow imidazolium chromophores, the hair color compositions of the present invention may include optional ingredients in order to further enhance the properties of the composition.

The hair color compositions described herein may be formed as thick liquid, cream, gel, emulsion, foam, aerosol mousse or as a solid form to which water is added to generate the oxidant and form a thickened vehicle suitable for hair coloring.

Optional Ingredients

Suitable optional ingredients include, but are not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof. Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The hair color compositions described herein may further comprise a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

In an embodiment, the solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least about 20%, alternatively from at least about 40%, alternatively from at least about 70%, by weight of the total composition. In an embodiment, the composition may comprise a total amount of organic solvents ranging from about 1% to about 30%, by weight of the total hair color composition.

Oxidizing Agent

The hair color composition described herein may comprise at least one source of an oxidizing agent. Exemplary oxidizing agents for use herein include water soluble peroxygen oxidizing agents. Water-soluble peroxygen oxidizing agents are well known in the art and include, but are not limited to, hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulfates and the like. These inorganic perhydrate salts may be incorporated as monohydrates, tetrahydrates etc. Alkyl and aryl peroxides, and or peroxidases, oxidases, and uricases and their substrates may also be used. Mixtures of two or more such oxidizing agents can also be used if desired. The oxidizing agents may be provided in aqueous solution or as a powder which is dissolved prior to use. In an embodiment, the oxidizing agents may be selected from the group consisting of hydrogen peroxide, percarbonate, persulfates and combinations thereof.

In an embodiment, the hair color composition may comprise from about 0.1% to about 20% by weight, or from about 1% to about 15% by weight, or from about 2% to about 10% by weight of the oxidizing agent.

A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Exemplary sources of carbonate ions, carbamate and hydrocarbonate ions are sodium hydrogen carbonate, potassium hydrogen carbonate, ammonium carbamate, and mixtures thereof.

The oxidizing agent may comprise from 0.1% to 15% by weight, or from 1% to 10% by weight, or from 1% to 8% by weight of a hydrogen carbonate ion; and from 0.1% to 10% by weight, or from 1% to 7% by weight, or from 2% to 5% by weight of the oxidizing agent of a source of hydrogen peroxide.

Alkalizing Agent

The hair color composition described herein may further comprise an alkalizing agent as known in the art. Any alkalizing agent known in the art may be used such as ammonia, alkanolamines for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. In an embodiment, the alkalizing agent may be ammonia and/or monoethanolamine.

The hair color compositions described herein may comprise from about 0.1% to about 10%, alternatively from about 0.5% to about 6%, alternatively from about 1% to about 4% by weight of the alkalizing agent relative to the total weight of the composition.

The hair colorant compositions described above may have a pH of from 7 to 12, alternatively from 8 to 11. For embodiments comprising a peroxymonocarbonate ion, the pH may be up to and including pH 9.5, alternatively from 7.5 to 9.5, alternatively from 8.4 to 9.5, alternatively from 8.5 to 9.4, alternatively 9.0, and alternatively 9.3.

Any sub-components of the hair color compositions, such as a tint composition or an oxidizing composition, may have a different pH from the hair colorant composition. For example, if the tint composition comprises an alkalizing agent, the tint composition will have an alkaline pH, such as higher than 7. In an embodiment, the oxidizing composition may comprise an acidic pH of less than 7.

When the hair color composition described herein is obtained by mixing a developer and a tint composition prior to use, the alkalizing agent is generally present in the tint composition.

Oxidative Dye Precursors

In addition to the direct dye compounds described herein, the hair color composition may further comprise one or more oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

In an embodiment, the hair color composition may comprise a total amount of oxidative dye precursors ranging up to about 12%, alternatively from about 0.1% to about 10%, alternatively from about 0.3% to about 8%, alternatively from about 0.5% to about 6%, by weight of the total composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, (2,3-diamino-6,7-dihydro-1H,5H-pyrazolo[1,2-a]pyrazol-1-one dimethanesulfonate), 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminoethane, 2[(3-aminopyrazolo[1,5-a]pyridin-2-yl) oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the hair color composition described herein is obtained by mixing a tint composition and a developer composition, the primary intermediates and couplers may be incorporated into the tint composition.

Additional Direct Dyes

The hair color composition may further comprise additional compatible direct dyes, in an amount sufficient to provide additional coloring, particularly with regard to intensity. In an embodiment, the composition may comprise a total amount of direct dyes ranging from about 0.05% to about 4%, by weight of the total composition.

Suitable direct dyes include but are not limited to: HC Yellow 17, HC Blue 18, HC Yellow 16, HC Red 18, Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N- propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the hair color composition is obtained by mixing a tint composition and a developer composition, the additional direct dyes may be incorporated into the tint composition.

Chelants

The hair color composition described herein may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

In an embodiment, the hair color composition may comprise a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant in the context of chelants all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—PO3H2) or its derivative —PO3R2, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylenediamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the hair color composition is obtained by mixing a tint composition and a developer composition, the chelants may be incorporated in the tint composition and/or in the developer composition. A chelant may be present in the developer composition for stability.

Radical Scavengers

The hair color compositions described herein may comprise a radical scavenger. As used herein the term radical scavenger refers to a species that can react with a radical, to convert the radical species by a series of fast reactions to an unreactive or less reactive species. The radical scavenger may also be selected such that it is not an identical species as the alkalising agent and is present in an amount sufficient to reduce the damage to the hair during the colouring/ bleaching process. The compositions described herein can comprise a radical scavenger from about 0.1% to about 10%, alternatively from about 1% to about 7% by weight of the radical scavenger relative to the total weight of the composition.

Suitable radical scavengers for use herein may be selected from the classes of alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)-pyrazol-5-one, 1,3-diphenyl-pyrazol-5-one, methyl pyrazol-5-one-3-carboxylate, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof. In some embodiments, the inventive compositions may comprise glycine, sarcosine, lysine, serine, 2-methoxyethylamine, glucosamine, glutamic acid, morpholine, piperidine, ethylamine, 3-amino-1-propanol, or mixtures thereof.

pH Modifiers and Buffering Agents

The hair color compositions described herein may further comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The hair color compositions described herein may further comprise a thickener in an amount sufficient to provide the composition with a viscosity so that it can be readily applied to the hair without unduly dripping off the hair and causing mess.

In an embodiment, the hair color compositions may comprise a total amount of thickeners ranging from at least about 0.1%, alternatively at least about 1%, alternatively at least about 10%, alternatively at least about 20%, by weight of the total composition.

Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof. Commercially available anionic materials include those sold as Sepigel 305 by Seppic.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (XV) below $$CH_2=C(R1)CH_2OBnR \qquad (XV)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (XVI) below $$CH_2=C(R1)COOH \qquad (XVI)$$

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (XVII) below CH2=C(R1)COOBnR2 (XVII)

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (XVIII) below

CH2=C< (XVIII)

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

In an embodiment, the associative polymers may comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid can be acrylic acid, methacrylic acid or itaconic acid. Commercially available materials include those sold as Aculyn-22 by Rohm & Haas; Permulen TR1, Carbopol 2020, Carbopol Ultrez-21/-30 by Noveon, Structure 2001/3001 by National Starch. Other exemplary associative polymers include polyether polyurethane, commercially available as Aculyn-44/-46 by Rohm and Haas. Further exemplary associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/1382/2984/5984 by Noveon, Synthalen M/Synthalen L/Synthalen K/Synthalen CR by 3V, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and bio-polysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., all three being incorporated herein by reference. An exemplary polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie Another exemplary polysaccharide is hydroxypropyl starch derivative, particularly hydroxypropyl starch phosphate, commercially available as Structure XL® by National Starch, a hydrophobically modified cellulose derivative, commercially available as Structure® Cel 500 HM by AkzoNobel.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), polyvinylpyrrolidone (Povidone, FlexiThix™), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphiphilic polymers comprising at least one fatty chain and at least one hydrophilic unit selected from polyether urethanes comprising at least one fatty chain, blends of Ceteth—10 phosphate, Dicetyl phosphate and Cetearyl alcohol (available as Crodafos CES), and mixtures thereof.

Salt

In an embodiment, cosmetically acceptable salt, such as ammonium, sodium or potassium salts with appropriate counter ions, may be added to the hair color compositions described herein to act as leveling agents to minimize patchy coloring results.

Carbonate Ion Sources

The hair color compositions described herein may further comprise a source of carbonate ions, carbamate ions, hydrogen carbonate ions, and mixtures thereof in a sufficient amount to reduce damage to the hair during the coloring process.

In an embodiment, the hair color compositions may comprise a total amount of a carbonate ion source ranging from about 0.1% to about 15%, alternatively from about 0.1% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The hair color compositions described herein may further comprise a conditioning agent, and/or be used in combination with a composition comprising a conditioning agent.

In an embodiment, the hair color compositions may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials may be cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane $(Si(CH_3)_2—O)$ units within the polymer chain, with either terminal, graft, or a mixture of terminal and graft amino-functional groups. Example functional groups are not limited to aminoethylaminopropyl, aminoethylaminoisobutyl, aminopropyl. In the case of graft polymers, the terminal siloxane units can be $(CH_3)_3Si—O$, $R_{12}(CH_3)_2Si—O$, where $R_{12}$ can be either OH or $OR_{13}$, where $R_{13}$ is a C1-C8 alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alkyl chains. Commercially available materials are known as methoxy PEG/PPG-7/3 Aminopropyl Dimethicone (e.g. Abil Soft AF100, by Degussa), or as Bis(C13-15 Alkoxy) PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5 \times 10^6$, alternatively from about 1000 to about $3 \times 10^6$. The cationic polymers can be selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinyl-lactams such as vinlypyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); copolymers of vinyl pyrrolidone and dialkyaminoalkyl acrylates or methacrylates, including polymers known as Polyquaternium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulfate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epoxypropyl/diethylenetriamine.

5) Cyclopolymers of dialkdiallylamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [—N+(R1)(R2)-A1-N+(R3)(R4)-B1-] [2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulfur atoms and sulfoxide, sulfone, disulfide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax).

7) Polyquaternary ammonium polymers comprising repeating units of formula [—N+(R6)(R7)-(CH2)r-NH—CO—(CH2)q-(CO)t-NH—(CH2)s-N+(R8)(R9)-A-][2X—], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2-. Suitable examples include: polymers known as polyquaternium-2, where r=s=3, q=0, t=0, R6, R7, R8 and R9 are methyl groups, and A is —CH2-CH2-O—CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-CH2-O—CH2-CH2; as Polyquaternium 18, where r=s=3, q=7, t=1 R6, R7, R8 and R9 are methyl groups, and A is —CH2-CH2-O—CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370/FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4) alkyltri(C1-C4) alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutyl, aminopropyl. In the case of graft polymers, the terminal siloxane units can either be (CH3)3Si—O or R12 (CH3)2Si—O, where R12 can be either OH or OR13, where R13 is a C1-C8 alkyl group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alkyl group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alkyl chains. For example products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

In an embodiment, the cationic polymer is selected from the group consisting of polyquaternium 37, polyquaternium 7, polyquaternium 22, polyquaternium 87, and mixtures thereof; alternatively from the group consisting of polyquaternium 37, polyquaternium 22, and mixtures thereof.

Surfactants

The hair color compositions described herein may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

In an embodiment, the hair color compositions may comprise a total amount of surfactants ranging from about 0.01% to about 60%, alternatively from about 0.05% to about 30%, alternatively from about 0.1% to about 25%, alternatively from about 0.1% to about 20%, by weight of the total composition.

The compositions may comprise a mixture of an anionic surfactant and an amphoteric surfactant with one or more nonionic surfactants. The composition may comprise a total amount of anionic surfactant ranging from about 0.01% to about 20%, alternatively from about 0.05% to about 15%, alternatively from about 0.1% to about 15%, by weight of the total composition; and a total amount of amphoteric and/or nonionic components, which may range independently from each other from about 0.01% to about 15%, alternatively from about 0.05% to about 10%, alternatively from about 0.1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, a-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides having from 2 to 30 mol of ethylene oxide and their monoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido($C_1$-$C_6$)alkylbetaines or ($C_8$-$C_{20}$)alkylamido($C_1$-$C_6$)alkylsulfobetaines. Among the amine derivatives, mention may be made of the products sold as Miranol, as described, for example, in U.S. Pat. Nos. 2,528,378 and 2,781,354 and having the structures of: $R_2$—CONHCH$_2$CH$_2$—N$^+$(R$_3$)(R$_4$)(CH$_2$COO$^-$), (XIX) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—CONHCH$_2$CH$_2$—N(B)(C) (XX) wherein B represents CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium caproamphodiac-etate, disodium cocoamphodipropionate, disodium lauroamphodipropionate, disodium caprylamphodipropionate, disodium caproamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary ammonium salts of general formula (XXI) below:

(XXI)

wherein X$^-$ is an anion chosen from halides (chloride, bromide and iodide), ($C_2$-$C_6$)alkyl sulfates, such as methyl sulfate, phosphates, alkyl and alkylaryl sulfonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulfur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulfur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from ($C_{12}$-$C_{22}$)alkylamido($C_2$-$C_6$)alkyl and ($C_{12}$-$C_{22}$) allylacetate radicals. A suitable cationic surfactant is, for example, a dicetyldimethyl ammonium salt (for example chloride);

B) Quaternary ammonium salts of imidazolinium of formula (XXII) below:

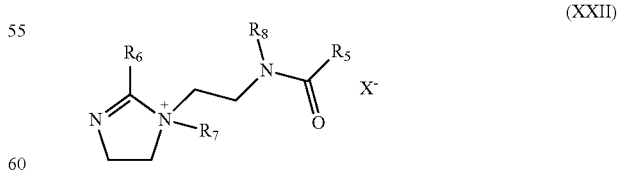

(XXII)

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and $X^-$ is an anion chosen from halides, phosphates, acetates, lactates, alkyl sulfates, alkyl sulfonates and alkylaryl sulfonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (XXIII):

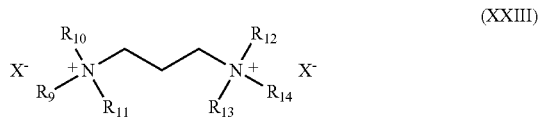

(XXIII)

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulfates. Such diquaternary ammonium salts, for example, include propanetallowdiammonium dichloride.

D) Quaternary ammonium salts comprising at least one ester function, of formula (XXIV) below:

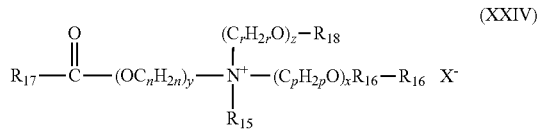

(XXIV)

in which: R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X— is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XXXXI) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

The following are examples of the synthesis of various dye compounds as described herein:

Example 1

In example 1, (E)-2-((5-amino-1-methyl-1H-pyrazol-4-yl)diazenyl)-1,3-bis(3-ammoniopropyl)-1H-imidazol-3-ium 2,2,2-trifluoroacetate is prepared from 2-aminoimidazole and 1-Methyl-1H-pyrazol-5-amine.

Synthesis of (E)-4-((1H-imidazol-2-yl)diazenyl)-1-methyl-1H-pyrazol-5-amine

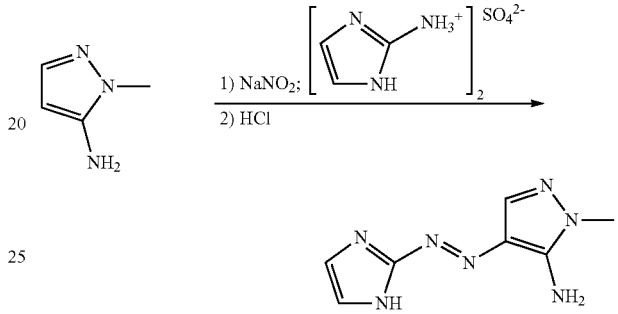

Concentrated HCl (17.16 mL, 206 mmol) and 1H-imidazol-2-aminium sulfate (6.67 g, 25.1 mmol) were added to a 150 mL Erlenmeyer flask and cooled in ice/methanol bath to <0° C. Sodium nitrite (3.55 g, 51.48 mmol) is dissolved in ca. 20 mL of water and added dropwise to the solution above keeping the temperature below 5° C.

In a separate flask sodium carbonate (27.2 g, 257 mmol) is dissolved in 200 mL of water. 1-Methyl-1H-pyrazol-5-amine (5 g, 51.48 mmol) is added. Upon cooling and stirring the solution became slushy. The 2-aminoimidazole containing solution is added to the 1-methyl-5-aminopyrazole solution, keeping the temperature below 5° C. Following complete addition the reaction mixture is kept cold and stirred for ca. 1 hour. Ethyl acetate (1 L) is added to the reaction mixture and the mixture is transferred to 2 L separatory funnel. The ethyl acetate is collected, and the aqueous phase is extracted twice more with ethyl acetate (2×1 L). The extracts were combined and evaporated providing 5.0 g of a black semi-solid. The crude (E)-4-((1H-imidizol-2-yl)diazenyl)-1-methyl-1H-pyrazol-5-amine is purified by column chromatography.

Synthesis of N-(4-bromopropyl)-2,2,2-trifluoroacetamide

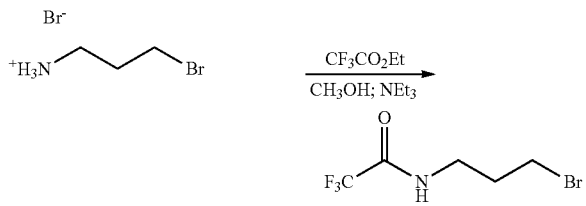

To a mixture of 4-bromo-1-propylamine hydrobromide (8.76 g) and ethyl trifluoroacetate (6.82 g) in 100 mL of methanol at 0° C. is added 6.06 g of trimethylamine dropwise, carefully controlling the temperature. The reaction solution is warmed to room temperature and stirred overnight. Solvent is evaporated under vacuum and the residue is dissolved in methylene chloride. The solution is washed with water and 1M HCl and concentrated. The crude N-(4-bromopropyl)-2,2,2-trifluoroacetamide is used in the next step without further purification.

Synthesis of (E)-2-((5-amino-1-methyl-1H-pyrazol-4-yl)diazenyl-1,3-bis(3-(2,2,2-trifluoroacetamido)propyl-1H-imidazol-3-ium bromide

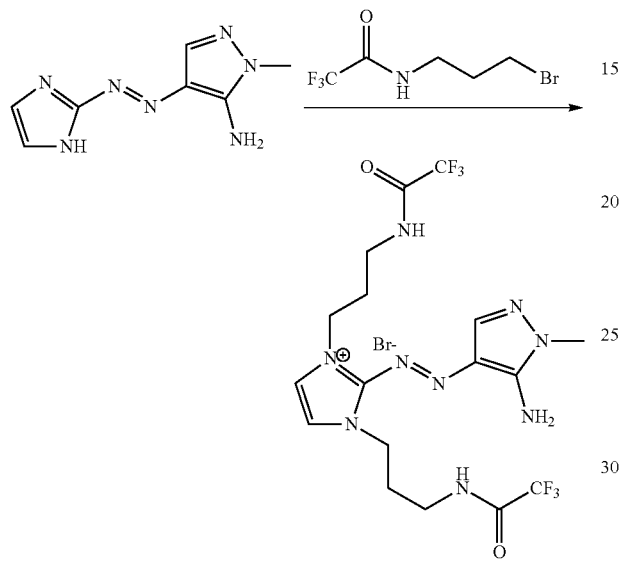

(E)-4-((1H-imidizol-2-yl)diazenyl)-1-methyl-1H-pyrazol-5-amine (1.23 g, 6.8 mmol) is dissolved in acetonitrile. Sodium bicarbonate (1.72 g, 20.5 mmol) is added, followed by 3-bromopropyltrifluroroacetamide (4.8 g, 20.5 mmol). The mixture is refluxed for 16 hours. Additional 3-bromopropyltrifluoroacetamide (1.6 g, 6.8 mmol) is added and reflux continued for 24 hours. The hot reaction mixture is filtered thru cellulose filter paper and evaporated. The crude (E)-2-((5-amino-1-methyl-1H-pyrazol-4-yl)diazenyl-1,3-bis(3-(2,2,2-trifluoroacetamido)propyl-1H-imidazol-3-ium bromide is carried directly to the deprotection reaction.

Synthesis of (E)-2-((5-amino-1-methyl-1H-pyrazol-4-yl)-1,3-bis(3-ammoniopropyl)-1H-imidazol-3-ium 2,2,2-trifluoroacetate

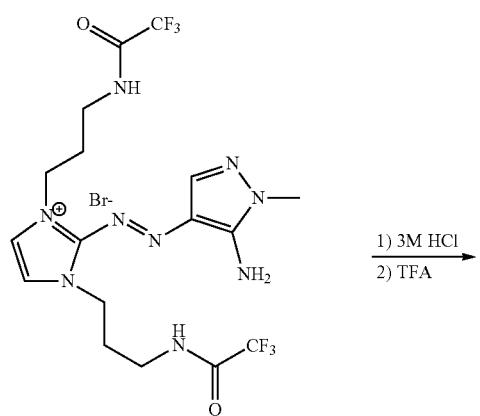

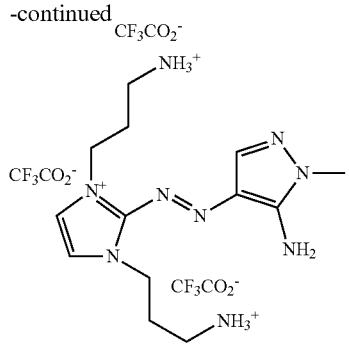

Crude (E)-2-((5-amino-1-methyl-1H-pyrazol-4-yl)diazenyl-1,3-bis(3-(2,2,2-trifluoroacetamido)propyl-1H-imidazol-3-ium bromide is dissolved in 10 mL of 3M HCl and refluxed overnight. The solvent is evaporated and the crude product is chromatographed on a reverse phase C-18 column providing 500 mg of pure (E)-2-((5-amino-1-methyl-1H-pyrazol-4-yl)diazenyl)-1,3-bis(3-ammoniopropyl)-1H-imidazol-3-ium 2,2,2-trifluoroacetate.

Example 2

In Example 2, (E)-2-((5-amino-1-hexyl-1H-pyrazol-4-yl)diazenyl)-1,3-bis(3-aminopropyl)-1H-imidazol-3-ium bromide dihydrochloride is prepared from acrylonitrile and 2-aminoimidazole.

Synthesis of 3-hydrazinylpropanitrile

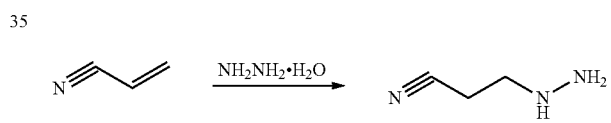

64-65% Hydrazine hydrate (1:1) (77 g, 0.992 mol) is dissolved in 1-propanol (100 mL) and cooled in ice-methanol to −5° C. Acrylonitrile (55.65 g, 1.057 mol) is added dropwise keeping the internal temperature below 0° C. The reaction is stirred at −5° C. for 30 minutes, and allowed to warm to room temperature for 1 hour. This material, 3-hydrazinylpropanitrile, is used directly in the next reaction.

Synthesis of (E)-3-(2-hexylidenehydrazinyl)propanenitrile

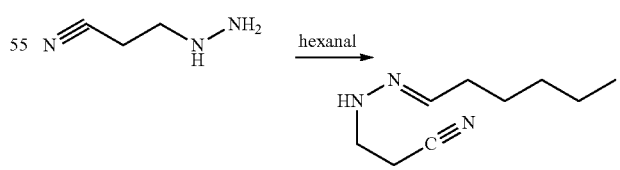

1-hexanal (105 g, 1.05 mol) is added dropwise at room temperature to the freshly prepared solution of 3-hydrazinylpropanitrile from the previous reaction, keeping the internal temperature below 30° C. The solution is stirred for 1 hour at room temperature followed by solvent evaporation providing (E)-3-(2-hexylidenehydrazinyl)propanenitrile.

Synthesis of 1-hexyl-1H-pyrazol-5-amine

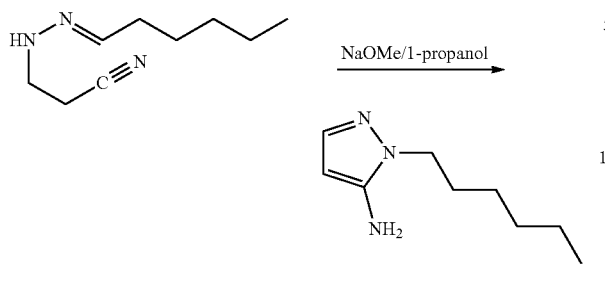

(E)-3-(2-hexylidenehydrazinyl)propanenitrile (72 g, 0.415 mol) is added to a 500 mL round bottom flask along with 75 mL of 1-propanol. Sodium methoxide, 25% (7.5 g, 34.7 mmol) is added and the mixture heated to reflux for 2-3 hours. The 1-propanol is evaporated and the residue is distilled via short path distillation collecting 35 g of material at a wide range of temperatures (84-140C). The 35 g were chromatographed on 2000 g of silica gel with very slow elution. The combined pure fractions provided 1-hexyl-1H-pyrazol-5-amine (29.5 g, 42%).

Synthesis of (E)-4-((1H-imidazol-2-yl)diazenyl)-1-hexyl-1H-pyrazol-5-amine

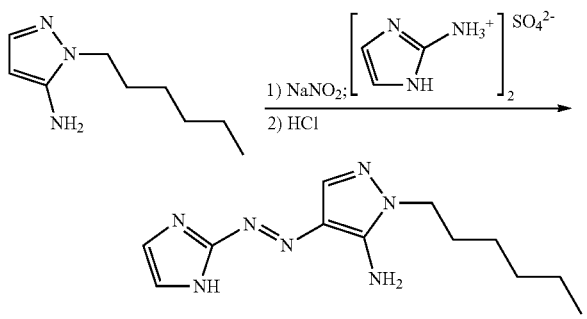

1H-Imidazol-2-aminium sulfate (4.15 g, 15.7 mmol) is dissolved in concentrated HCl (10 mL, 119.56 mmol) and cooled in an ice-methanol bath to $-5°$ C. Sodium nitrite (2.27 g, 32.88 mmol) is dissolved in minimum water and added slowly to the 2-aminoimidazole keeping temperature below $0°$ C. This is the diazonium salt and it is maintained at $<0°$ C.

In a separate flask, 1-(hexyl)-5-aminopyrazole (5 g, 29.89 mmol) is dissolved in 5 mL of ethanol and water is added until just before the cloud point is reached. Sodium carbonate (15.8 g, 149.45 mmol) is added to this solution. The cold diazonium salt is added to the slushy solution of 1-hexyl-1H-pyrazol-5-amine resulting in a black mixture. The internal temperature drops slightly during addition due to the colder diazonium salt thus the diazonium salt can be added at a moderate rate. Following complete diazo addition the mixture is stirred at $0°$ C. for 1 hour and then warmed to room temperature and stirred for 2 hours. The reaction mixture is diluted with water. The black aqueous phase is transferred to a separatory funnel and extracted with ethyl acetate (2×500 mL). The resulting ethyl acetate extracts are combined and evaporated providing 6 g of material. This material is chromatographed on silica gel. The combined pure fractions provide (E)-4-((1H-imidazol-2-yl)diazenyl)-1-hexyl-1H-pyrazol-5-amine (4 g, 51%).

Synthesis of (E)-2-((5-amino-1-hexyl-1H-pyrazol-4-yl)diazenyl)-1,3-bis(3-(2,2,2-trifluoroacetamido)propyl)-1H-imidizol-3-ium bromide

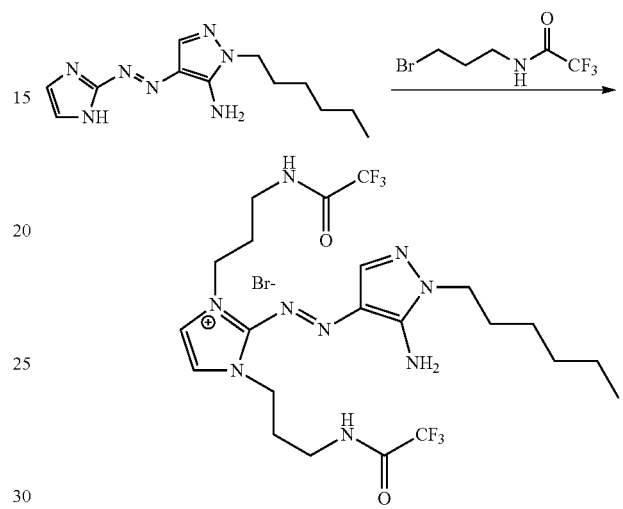

(E)-4-((1H-imidazol-2-yl)diazenyl)-1-hexyl-1H-pyrazol-5-amine (14.43 g, 55.22 mmol) is dissolved in 300 mL of acetonitrile. Sodium bicarbonate (10.20 g, 121.5 mmol) and 3-bromopropyl trifluoroacetamide (28.43 g, 121.5 mmol) were added and the reaction heated to reflux. The reaction is refluxed further for several days along with additional 3-bromopropyl trifluoroacetamide (12 g) and 300 mL of additional acetonitrile. The mixture is evaporated providing 54 g of material. This is chromatographed on silica gel columns yielding 19.5 g (54%) of pure (E)-2-((5-amino-1-hexyl-1H-pyrazol-4-yl)diazenyl)-1,3-bis(3-(2,2,2-trifluoroacetamido)propyl)-1H-imidizol-3-ium bromide.

Synthesis of (E)-2-((5-amino-1-hexyl-1H-pyrazol-4-yl)diazenyl)-1,3-bis(3-aminopropyl)-1H-imidizol-3-ium bromide dihydrochloride

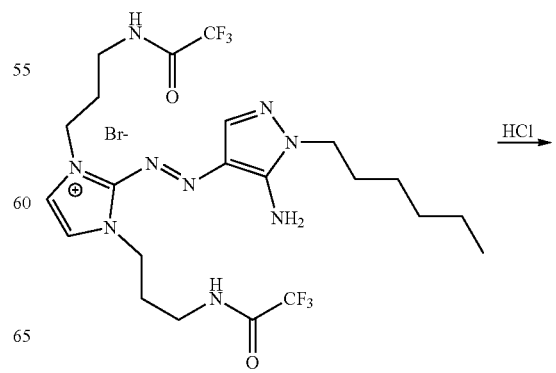

-continued

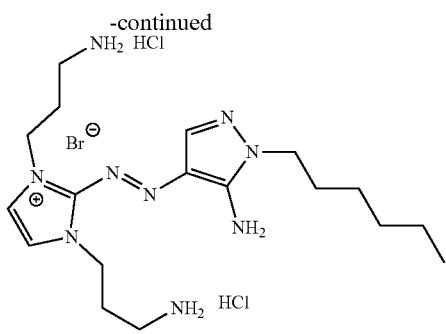

(E)-2-((5-amino-1-hexyl-1H-pyrazol-4-yl)diazenyl)-1,3-bis(3-(2,2,2-trifluoroacetamido)propyl)-1H-imidizol-3-ium bromide (19.5 g, 30.1 mmol) is suspended in 80 mL (0.9 mol) of concentrated HCl and refluxed for 2 hours. The hydrochloric acid is evaporated and the product triturated with ethyl acetate (250 mL). This suspension is filtered under inert atmosphere providing (E)-2-((5-amino-1-hexyl-1H-pyrazol-4-yl)diazenyl)-1,3-bis(3-aminopropyl)-1H-imidizol-3-ium bromide dihydrochloride (14.7 g, 92% yield).

Example 3

In Example 3, (E)-2-((5-amino-1-(2-hydroxyethyl)-1H-pyrazol-4-yl)diazenyl)-1,3-bis(3-ammoniopropyl)-1H-imidazol-3-ium bromide dichloride is prepared from 2-(5-amino-1H-pyrazol-1-yl)ethan-1-ol and 1H-imidazol-2-amine.

Synthesis of (E)-2-(4-((1H-imidazol-2-yl)diazenyl)-5-amino-1H-pyrazol-1-yl)ethan-1-ol

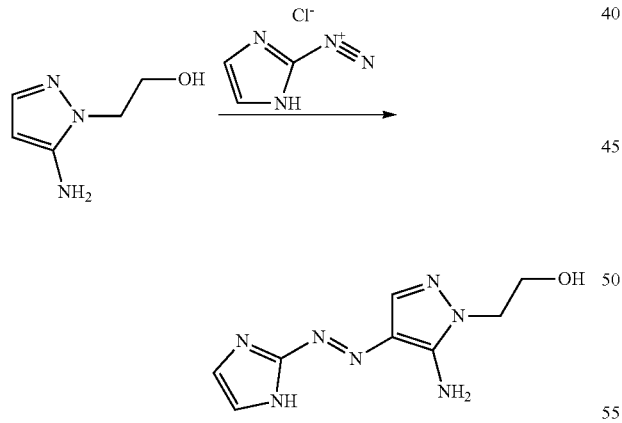

2-Aminoimidazole (5.0 g, 37.8 mmol) is dissolved in concentrated HCl (12.6 mL, 151 mmol) and cooled in an ice-methanol bath to −5° C. Sodium nitrite (2.61 g, 37.8 mmol) is dissolved in the minimum of water (<4 mL) and added slowly to the 2-aminoimidazole keeping temperature below 0° C. This is the diazonium salt and it is maintained at <0° C.

In a separate flask, 2-(5-amino-1H-pyrazol-1-yl)ethan-1-ol (5 g, 29.89 mmol) is dissolved in 5 mL of ethanol and water is added until just before the cloud point is reached. Sodium carbonate (19.96 g, 189.0 mmol) is added. The mixture is cooled in an ice-water bath to ca. 5° C. resulting in a solution having a slushy consistency. The cold diazonium salt is added to the slushy solution of the 2-(5-amino-1H-pyrazol-1-yl)ethan-1-ol resulting in a black mixture. Following complete diazo addition the mixture is stirred at 0° C. for 1 hour and allowed to warm to room temperature and then stirred for 2 hours. The reaction mixture is diluted with water. The black aqueous phase is extracted with cold ethyl acetate and then hot ethyl acetate (500 mL each) providing 3 g of material. The aqueous phase from the extraction is evaporated and triturated with ethyl acetate, which generated an additional 3 g of material. The combined 6 g is chromatographed on silica gel to provide pure (E)-2-(4-((1H-imidazol-2-yl)diazenyl)-5-amino-1H-pyrazol-1-yl)ethan-1-ol (1.26 g, 15%).

Synthesis of (E)-2-((5-amino-1-(2-hydroxyethyl)-1H-pyrazol-4-yl)diazenyl)-1,3-bis(3-(2,2,2-trifluoroacetamido) propyl)-1H-imidazol-3-ium bromide

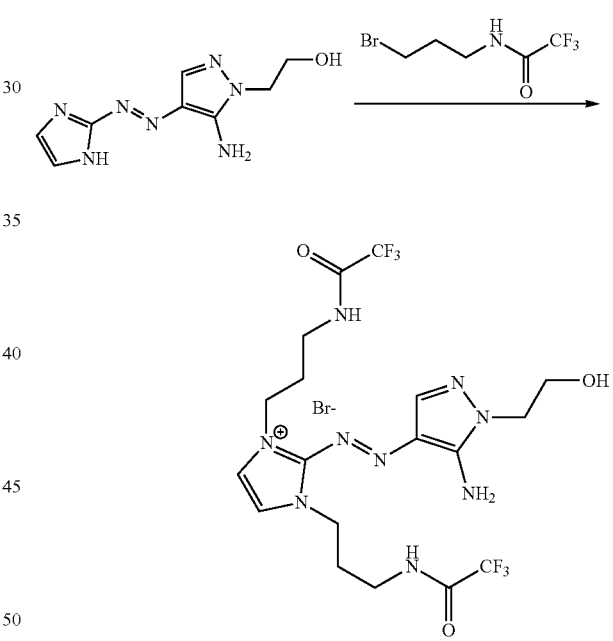

(E)-2-(4-((1H-imidazol-2-yl)diazenyl)-5-amino-1H-pyrazol-1-yl)ethan-1-ol (1.3 g, 5.88 mmol) is dissolved in 300 mL of acetonitrile. Sodium bicarbonate (0.99 g, 11.76 mmol) and N-(3-bromopropyl)-2,2,2-trifluoroacetamide (3.03 g, 12.94 mmol) were added and the reaction heated to reflux. Additional N-(3-bromopropyl)-2,2,2-trifluoroacetamide (1.0 g, 800 mg, and 1.0 g) is added at twenty-four hour intervals and reflux is continued for 24 hours. After 8 days the hot reaction mixture is filtered and the filtrate evaporated. The residue is chromatographed on silica gel to provide pure (E)-2-((5-amino-1-(2-hydroxyethyl)-1H-pyrazol-4-yl)diazenyl)-1,3-bis(3-(2,2,2-trifluoroacetamido) propyl)-1H-imidazol-3-ium bromide (1.2 g, 35% yield)

Synthesis of (E)-2-((5-amino-1-(2-hydroxyethyl)-1H-pyrazol-4-yl)diazenyl)-1,3-bis(3-ammoniopropyl)-1H-imidazol-3-ium bromide dichloride

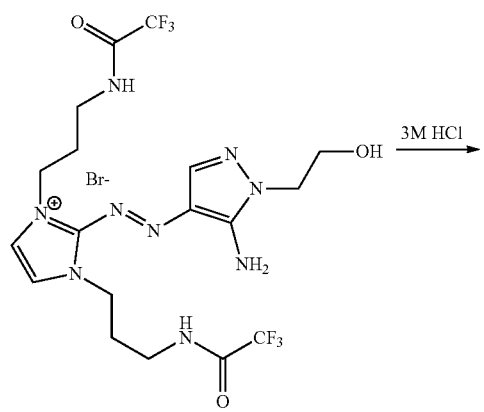

(E)-2-((5-amino-1-(2-hydroxyethyl)-1H-pyrazol-4-yl)diazenyl)-1,3-bis(3-(2,2,2-trifluoroacetamido) propyl)-1H-imidazol-3-ium bromide (1.2 g, 1.97 mmol) is suspended in 8 mL (24 mol) of 3M HCl and refluxed for 2 hours. The hydrochloric acid is evaporated and the product triturated with ethyl acetate (250 mL). This suspension is subsequently filtered under inert atmosphere, providing (E)-2-((5-amino-1-(2-hydroxyethyl)-1H-pyrazol-4-yl)diazenyl)-1,3-bis(3-ammoniopropyl)-1H-imidazol-3-ium bromide dichloride (0.90 g, 94% yield).

Example 4

In example 4, (E)-2-((5-amino-1-hexyl-1H-pyrazol-4-yl)diazenyl)-1-(3-ammoniopropyl)-3-methyl-1H-imidazol-3-ium bromide chloride is prepared from 2-aminoimidazole and 1-hexyl-1H-pyrazol-5-amine.

Synthesis of (E)-2-((5-amino-1-hexyl-1H-pyrazol-4-yl)diazenyl)-3-methyl-1-(3-(2,2,2-trifluoroacetamido)propyl)-1H-imidazol-3-ium bromide

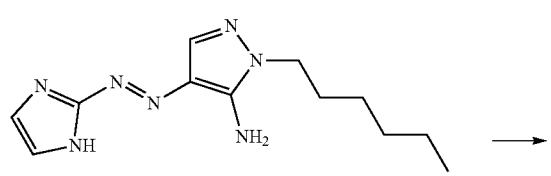

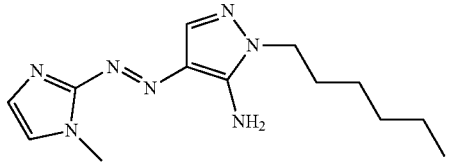

(E)-4-((1H-imidazol-2-yl)diazenyl)-1-hexyl-1H-pyrazol-5-amine (3.0 g, 11.48 mmol) is dissolved in 200 mL of acetonitrile. Sodium bicarbonate (2.89 g, 34.44 mmol) and iodomethane (4.88 g, 34.44 mmol) were added and the reaction heated to reflux for 3.25 hours. The hot reaction mixture is filtered to remove sodium bicarbonate and the solvent evaporated. The crude solid is chromatographed on silica gel to provide (E)-1-hexyl-4-((1-methyl-1H-imidazol-2-yl)diazenyl)-1H-pyrazol-5-amine (0.90 g, 28% yield).

Synthesis of (E)-2-((5-amino-1-hexyl-1H-pyrazol-4-yl)diazenyl)-3-methyl-1-(3-(2,2,2-trifluoroacetamido)propyl)-1H-imidazol-3-ium bromide

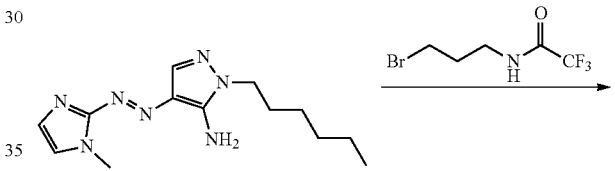

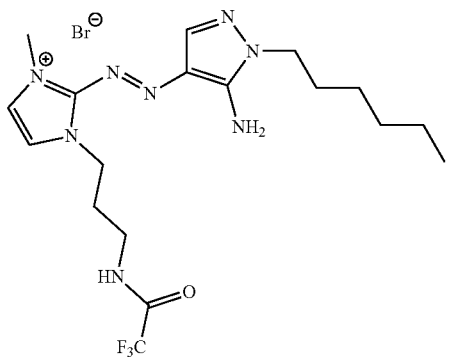

(E)-1-hexyl-4-((1-methyl-1H-imidazol-2-yl)diazenyl)-1H-pyrazol-5-amine (1.0 g, 3.67 mmol) is dissolved in 100 mL of acetonitrile. Sodium bicarbonate (0.34 g, 4.03 mmol) and N-(3-bromopropyl)-2,2,2-trifluoroacetamide (1.89 g, 8.06 mmol) were added and the reaction heated to reflux for 20 hours. The hot reaction mixture is filtered and the solvent evaporated. The crude product is chromatographed on silica gel to provide (E)-2-((5-amino-1-hexyl-1H-pyrazol-4-yl)diazenyl)-3-methyl-1-(3-(2,2,2-trifluoroacetamido)propyl)-1H-imidazol-3-ium bromide (1.01 g, 65% yield).

Synthesis of (E)-2-((5-amino-1-hexyl-1H-pyrazol-4-yl)diazenyl)-1-(3-ammoniopropyl)-3-methyl-1H-imidazol-3-ium bromide chloride

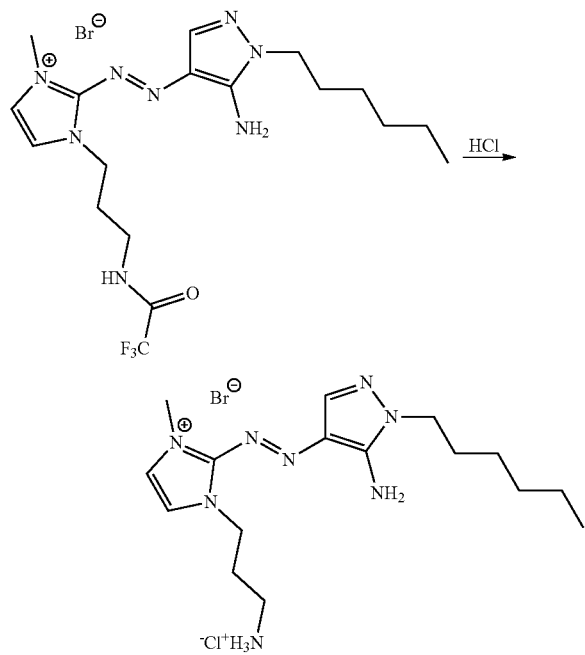

(E)-2-((5-amino-1-hexyl-1H-pyrazol-4-yl)diazenyl)-3-methyl-1-(3-(2,2,2-trifluoroacetamido)-propyl)-1H-imidazol-3-ium bromide (1.0 g, mmol) is suspended in 8 mL (24 mmol) of 3M HCl and refluxed for 2 hours. The hydrochloric acid is evaporated and the product triturated with ethyl acetate (250 mL). This suspension is filtered under inert atmosphere to provide (E)-2-((5-amino-1-hexyl-1H-pyrazol-4-yl)diazenyl)-1-(3-ammoniopropyl)-3-methyl-1H-imidazol-3-ium bromide chloride (0.710 g, 90% yield).

Example 5

In Example 5, (E)-2-((5-amino-1-hexyl-1H-pyrazol-4-yl)diazenyl)-1-(3-ammoniopropyl)-3-propyl-1H-imidazol-3-ium bromide chloride is prepared from 1-hexyl-1H-pyrazol-5-amine and 1H-imidazol-2-amine.

Synthesis of (E)-N-(3-(2-((5-amino-1-hexyl-1H-pyrazol-4-yl)diazenyl)-1H-imidazol-1-yl)propyl)-2,2,2-trifluoroacetamide

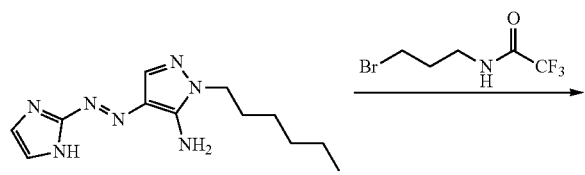

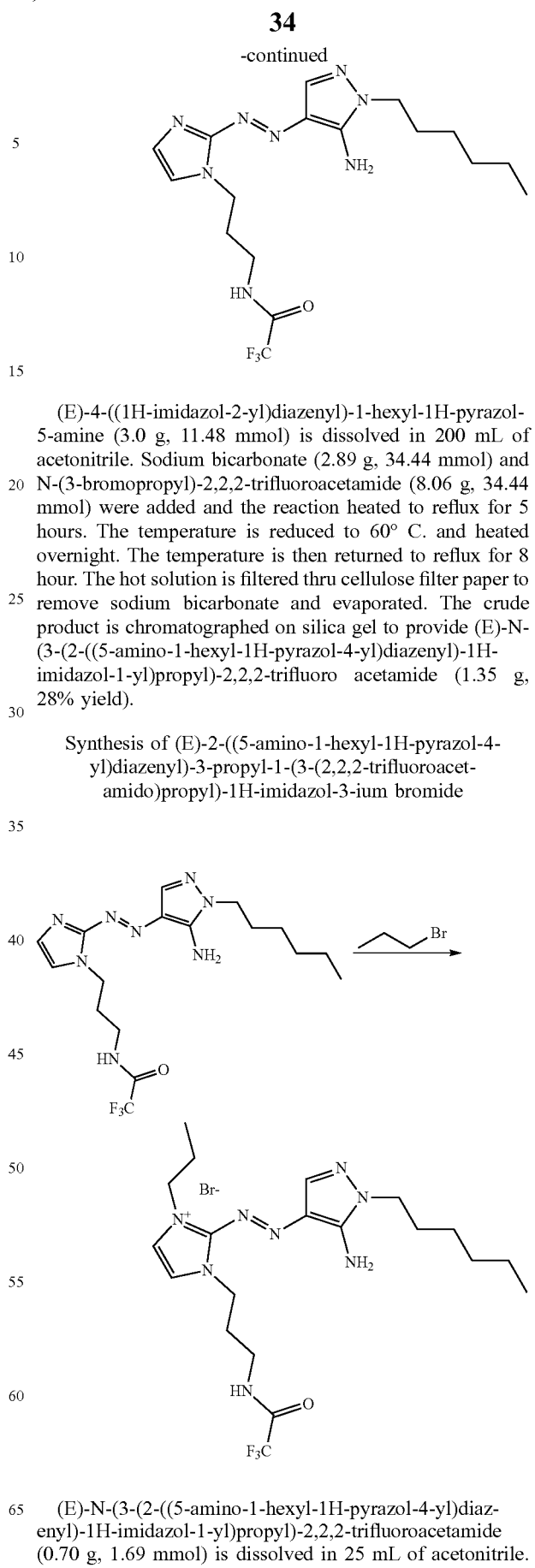

(E)-4-((1H-imidazol-2-yl)diazenyl)-1-hexyl-1H-pyrazol-5-amine (3.0 g, 11.48 mmol) is dissolved in 200 mL of acetonitrile. Sodium bicarbonate (2.89 g, 34.44 mmol) and N-(3-bromopropyl)-2,2,2-trifluoroacetamide (8.06 g, 34.44 mmol) were added and the reaction heated to reflux for 5 hours. The temperature is reduced to 60° C. and heated overnight. The temperature is then returned to reflux for 8 hour. The hot solution is filtered thru cellulose filter paper to remove sodium bicarbonate and evaporated. The crude product is chromatographed on silica gel to provide (E)-N-(3-(2-((5-amino-1-hexyl-1H-pyrazol-4-yl)diazenyl)-1H-imidazol-1-yl)propyl)-2,2,2-trifluoro acetamide (1.35 g, 28% yield).

Synthesis of (E)-2-((5-amino-1-hexyl-1H-pyrazol-4-yl)diazenyl)-3-propyl-1-(3-(2,2,2-trifluoroacetamido)propyl)-1H-imidazol-3-ium bromide (E)-N-(3-(2-((5-amino-1-hexyl-1H-pyrazol-4-yl)diazenyl)-1H-imidazol-1-yl)propyl)-2,2,2-trifluoroacetamide (0.70 g, 1.69 mmol) is dissolved in 25 mL of acetonitrile.

Sodium bicarbonate (200 mg, 2.38 mmol) and 1-bromopropane (1.0 g, 8.13 mmol) were added, followed by heating to reflux for 16 hours. The hot reaction mixture is filtered through cellulose paper to remove sodium bicarbonate. The crude product is chromatographed on silica gel providing pure (E)-2-((5-amino-1-hexyl-1H-pyrazol-4-yl)diazenyl)-3-propyl-1-(3-(2,2,2-trifluoroacetamido)propyl)-1H-imidazol-3-ium bromide (0.37 g, 48% yield).

Synthesis of (E)-2-((5-amino-1-hexyl-1H-pyrazol-4-yl)diazenyl)-1-(3-ammoniopropyl)-3-propyl-1H-imidazol-3-ium bromide chloride

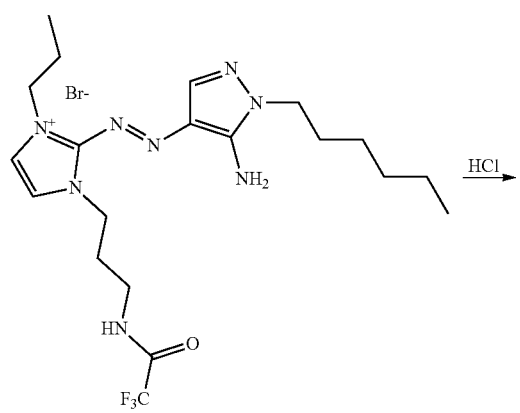

(E)-2-((5-amino-1-hexyl-1H-pyrazol-4-yl)diazenyl)-3-propyl-1-(3-(2,2,2-trifluoroacetamido)-propyl)-1H-imidazol-3-ium bromide (0.37 g, 0.688 mmol) is suspended in 3 mL (6.88 mmol) of 3M HCl and refluxed for 2 hours. The hydrochloric acid is evaporated and the product is triturated with ethyl acetate (250 mL). This suspension is filtered under inert atmosphere providing (E)-2-((5-amino-1-hexyl-1H-pyrazol-4-yl)diazenyl)-1-(3-ammoniopropyl)-3-propyl-1H-imidazol-3-ium bromide chloride (0.30 g, 90% yield).

Example 6

(E)-2-((5-amino-1-hexyl-1H-pyrazol-4-yl)diazenyl)-1-(3-ammoniopropyl)-3-hexyl-1H-imidazol-3-ium bromide chloride is prepared from 1-hexyl-1H-pyrazol-5-amine and 1H-imidazol-2-amine.

Synthesis of (E)-2-((5-amino-1-hexyl-1H-pyrazol-4-yl)diazenyl)-3-hexyl-1-(3-(2,2,2-trifluoroacetamido)propyl)-1H-imidazol-3-ium bromide

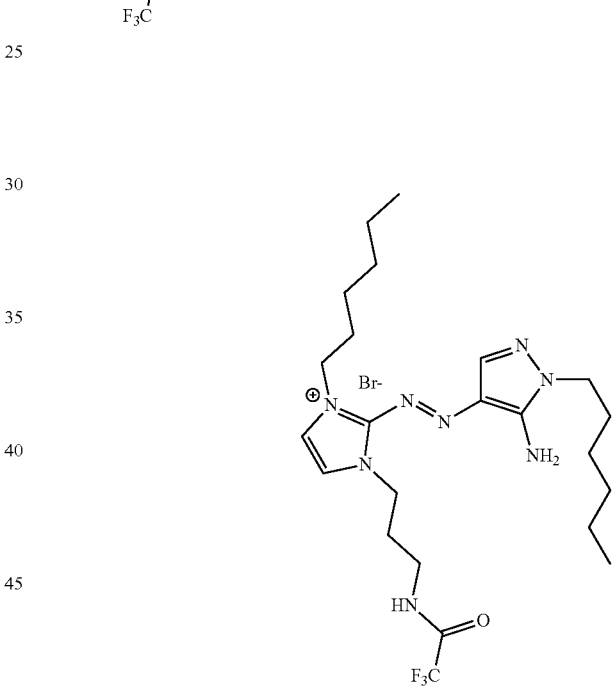

(E)-N-(3-(2-((5-amino-1-hexyl-1H-pyrazol-4-yl)diazenyl)-1H-imidazol-1-yl)propyl)-2,2,2-trifluoroacetamide (0.650 g, 1.57 mmol) is dissolved in 25 mL of acetonitrile. Sodium bicarbonate (200 mg, 2.38 mmol) and 1-bromohexane (1.035 g, 6.27 mmol) were added followed by heating to reflux for 16 hours. The hot reaction mixture is filtered through cellulose paper to remove sodium bicarbonate. The crude product is chromatographed on silica gel to provide pure (E)-2-((5-amino-1-hexyl-1H-pyrazol-4-yl)diazenyl)-3-hexyl-1-(3-(2,2,2-trifluoroacetamido)propyl)-1H-imidazol-3-ium bromide (0.30 g, 38% yield).

Synthesis of (E)-2-((5-amino-1-hexyl-1H-pyrazol-4-yl)diazenyl)-1-(3-ammoniopropyl)-3-hexyl-1H-imidazol-3-ium bromide chloride

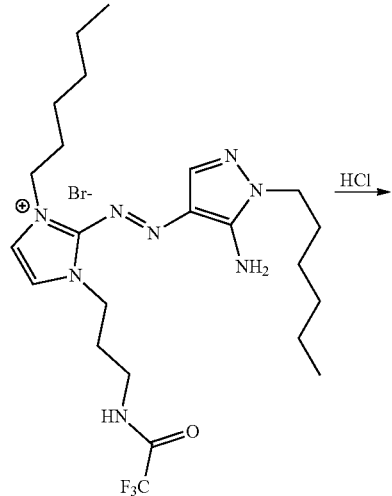

(E)-2-((5-amino-1-hexyl-1H-pyrazol-4-yl)diazenyl)-3-hexyl-1-(3-(2,2,2-trifluoroacetamido)propyl)-1H-imidazol-3-ium bromide (0.30 g, 0.518 mmol) is suspended in 3 mL (9 mmol) of 3M HCl and refluxed for 2 hours. The hydrochloric acid is evaporated and the product triturated with ethyl acetate (250 mL). This suspension is subsequently filtered under inert atmosphere providing (E)-2-((5-amino-1-hexyl-1H-pyrazol-4-yl)diazenyl)-1-(3-ammoniopropyl)-3-hexyl-1H-imidazol-3-ium bromide chloride (0.240 g, 90% yield).

Example 7

In Example 7, is prepared from t-butyl (3-hydroxypropyl) carbamate and 2-aminoimidazole.

Synthesis of t-butyl (3-oxopropyl)carbamate

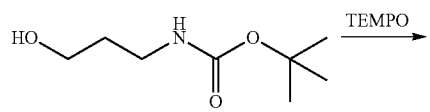

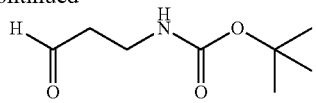

t-Butyl (3-hydroxypropyl)carbamate (15.3 g, 87.3 mmol) is dissolved in dichloromethane (200 mL) and 50 mL of water were added. Sodium bromide (9.43 g, 91.68 mmol) and sodium bicarbonate (8.07 g, 96.05 mmol) were added and the mixture cooled in ice/water bath to ca. 5° C. TEMPO (100 mg, 0.873 mmol) is added followed by the dropwise addition of sodium hypochlorite (102 mL, 113.5 mmol) at a moderate rate. The solution turns reddish-brown and this color fades to colorless as the reaction proceeds. Subsequently, additional (required) sodium hypochlorite is added in 10 mL portions until conversion is complete. The dichloromethane phase is collected and the aqueous phase is extracted one additional time with dichloromethane (250 mL) and the combined extracts washed with 10% sodium thiosulfate (100 mL). The dichloromethane portion is dried (MgSO$_4$), filtered and evaporated to afford t-butyl (3-oxopropyl)carbamate (12.5 g, 72 mmol) as a colorless oil.

Synthesis of tert-butyl (3-(5-amino-1H-pyrazol-1-yl)propyl)carbamate

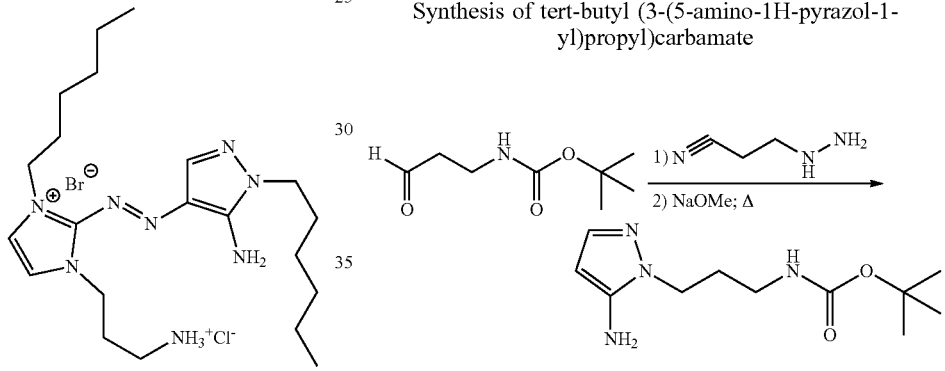

t-Butyl (3-oxopropyl)carbamate (2.32 g, 13.4 mmol) is dissolved in 1-propanol (20 mL). Cyanopropylhydrazine (1.14 g, 13.4 mmol) is dissolved in 10 mL of 1-propanol and added at room temperature. The internal temperature rises slightly to ca. 27° C. Stirring is continued overnight. 25% Sodium methoxide (1.0 g, 4.6 mmol) is added and the reaction heated to reflux for 2 hours. The mixture is evaporated, re-dissolved in dichloromethane and washed with water and saturated NaHCO$_3$ and the dichloromethane phase evaporated. The resulting oil is chromatographed on silica gel to afford t-butyl (3-(5-amino-1H-pyrazol-1-yl)propyl)-carbamate (0.750 g, 3.12 mmol).

Synthesis of (E)-N'-(1H-imidazol-2-yl)-N,N-dimethylformimidamide

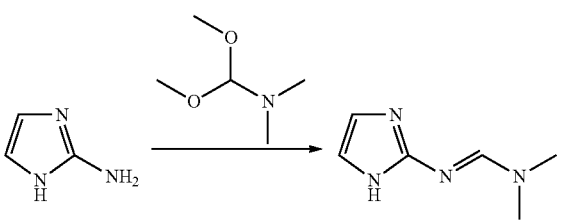

2-Aminoimidazole (13.3 g, 100 mmol) is dissolved in water. Sodium carbonate (15.93 g, 151 mmol) is added and the mixture stirred vigorously at room temperature for 1 hour, after which the water is evaporated. The resulting solid is suspended in ethanol, stirred for 1 hour and filtered through a pad of Celite. The filtrate is evaporated and then dissolved in dimethylformamide dimethylacetal (50 mL) and stirred overnight with ethyl acetate (150 mL). The suspended solids were collected by filtration affording (E)-N'-(1H-imidazol-2-yl)-N,N-dimethylformimidamide (9.64 g, 69.7 mmol) in sufficient purity to use in the subsequent alkylation reaction.

Synthesis of (E)-N'-(1-hexyl-1H-imidazol-2-yl)-N,N-dimethylformimidamide

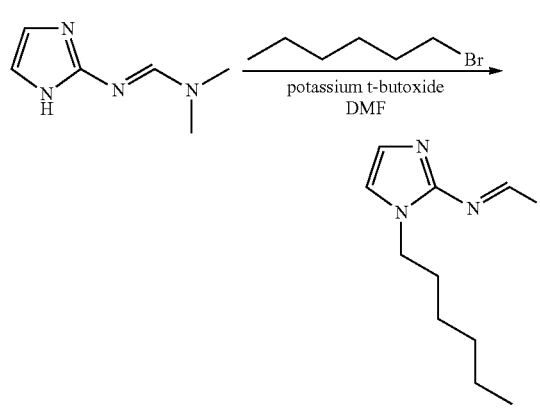

(E)-N'-(1H-imidazol-2-yl)-N,N-dimethylformimidamide (6.0 g, 43.43 mmol) is dissolved in dimethylformamide (100 mL). Potassium t-butoxide (9.75 g, 86.85 mmol) is added, followed by 1-bromohexane (10.75 g, 65.14 mmol) and the mixture stirred at 40° C. overnight. The reaction mixture is then quenched with water (50 mL), followed by acidification with concentrated HCl and extraction with dichloromethane. The combined dichloromethane extracts were dried (MgSO$_4$), filtered, and evaporated to afford a wet solid. The wet solid is heated to remove dimethylformamide affording (E)-N'-(1-hexyl-1H-imidazol-2-yl)-N,N-dimethylformimidamide (10.0 g, quantitative yield).

Synthesis of 1-hexyl-1H-imidazol-2-aminium chloride

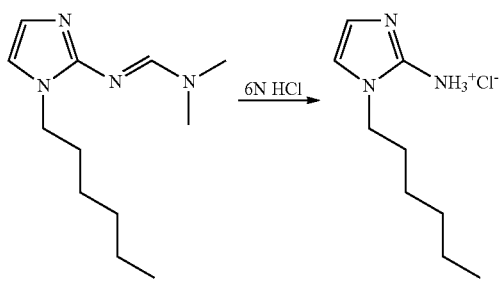

(E)-N'-(1-hexyl-1H-imidazol-2-yl)-N,N-dimethylformimidamide (9.66 g, 43.5 mmol) is suspended in 6N HCl (50 mL) and refluxed for 3 hours. The solvent is evaporated and the dry solid triturated with ethyl ether. The suspended solids were collected via filtration affording 1-hexyl-1H-imidazol-2-aminium chloride (8.3 g, 40.7 mmol) as an off-white solid.

Synthesis of t-butyl (E)-(3-(5-amino-4-((1-hexyl-1H-imidazol-2-yl)diazenyl)-1H-pyrazol-1-yl)propyl)carbamate

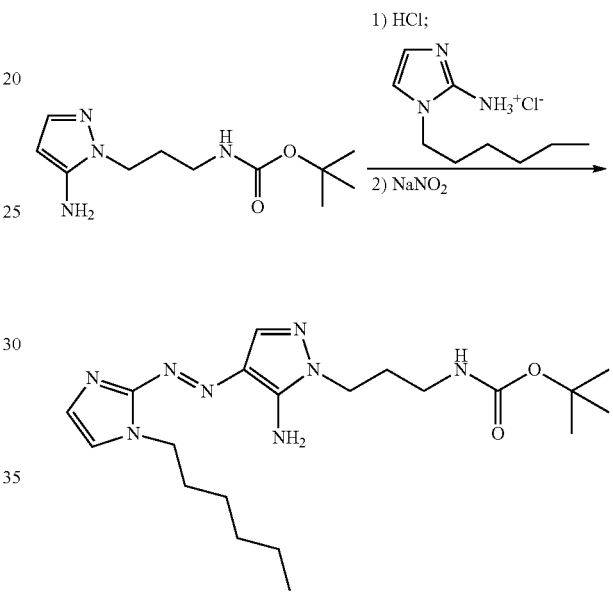

1-Hexyl-1H-imidazol-2-aminium chloride (1.58 g, 7.61 mmol) is dissolved in water (20 mL). Concentrated HCl (3.09 g, 30.44 mmol) is added and the mixture cooled in ice/methanol bath to −5° C. Sodium nitrite (0.57 g, 9.51 mmol) is dissolved in a minimum amount of water and added dropwise to the above mixture keeping the temperature below 0° C. The reaction mixture is allowed to stir for 30-60 minutes at <0° C. without allowing it to freeze. t-Butyl (3-(5-amino-1H-pyrazol-1-yl)propyl)carbamate (1.55 g, 6.45 mmol) is dissolved in methanol (50 mL) and water (200 mL). Sodium carbonate (4.09 g, 38.04 mmol) is added and the solution cooled in ice/water bath. The above diazonium salt is added dropwise to this solution keeping the temperature at 5° C. The reaction mixture is allowed to warm to room temperature over 1 hour then extracted with 2×500 mL of ethyl acetate. The combined ethyl acetate extracts were concentrated and the residue chromatographed on silica gel providing pure t-butyl (E)-(3-(5-amino-4-((1-hexyl-1H-imidazol-2-yl)diazenyl)-1H-pyrazol-1-yl)propyl)carbamate (0.90 g, 2.15 mmol).

Synthesis of (E)-2-((5-amino-1-(3-((tert-butoxycarbonyl)amino)propyl)-1H-pyrazol-4-yl)diazenyl)-1-hexyl-3-(3-(2,2,2-trifluoroacetamido)propyl)-1H-imidazol-3-ium bromide

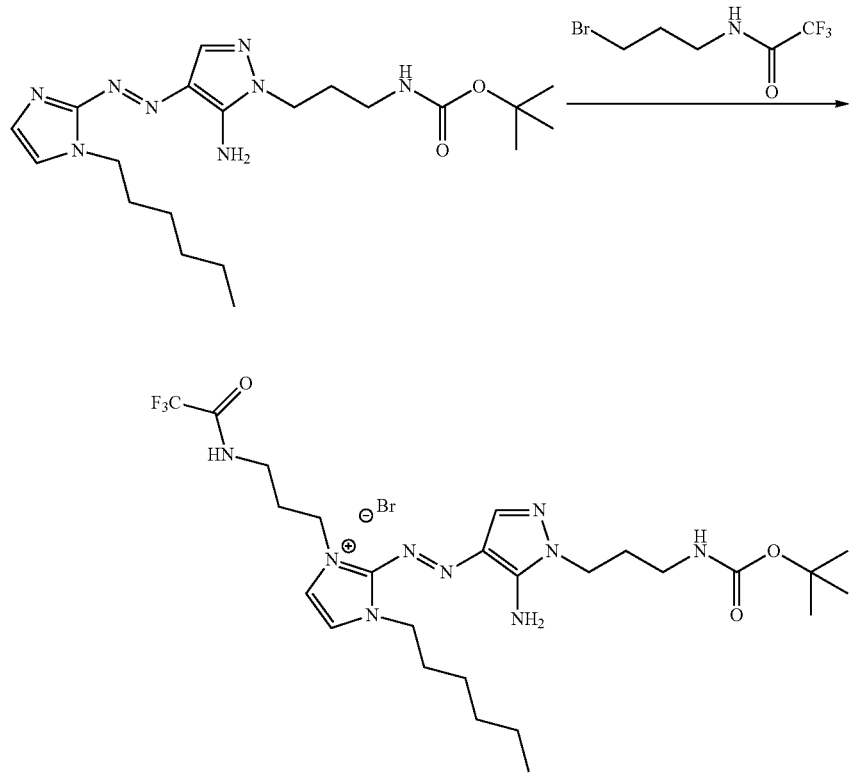 [SMILES: CCCCCCn1ccnc1/N=N/c1cnn(CCCNC(=O)OC(C)(C)C)c1N ; O=C(NCCCBr)C(F)(F)F ; CCCCCCn1cc[n+](CCCNC(=O)C(F)(F)F)c1/N=N/c1cnn(CCCNC(=O)OC(C)(C)C)c1N ; [Br-]]

t-Butyl (E)-(3-(5-amino-4-((1-hexyl-1H-imidazol-2-yl)diazenyl)-1H-pyrazol-1-yl)propyl)carbamate (0.85 g, 2.03 mmol) is suspended in acetonitrile (50 mL). N-(3-bromopropyl)-2,2,2-trifluoroacetamide (0.62 g, 2.63 mmol) added, followed by sodium bicarbonate (0.201 g, 2.40 mmol) and the mixture refluxed overnight. The crude product is chromatographed on silica gel to afford pure (E)-2-((5-amino-1-(3-((t-butoxycarbonyl)amino)propyl)-1H-pyrazol-4-yl)diazenyl)-1-hexyl-3-(3-(2,2,2-trifluoro acetamido)propyl)-1H-imidazol-3-ium bromide (1.0 g, 1.53 mmol).

Synthesis of (E)-2-((5-amino-1-(3-ammoniopropyl)-1H-pyrazol-4-yl)diazenyl)-3-(3-ammoniopropyl)-1-hexyl-1H-imidazol-3-ium bromide dichloride

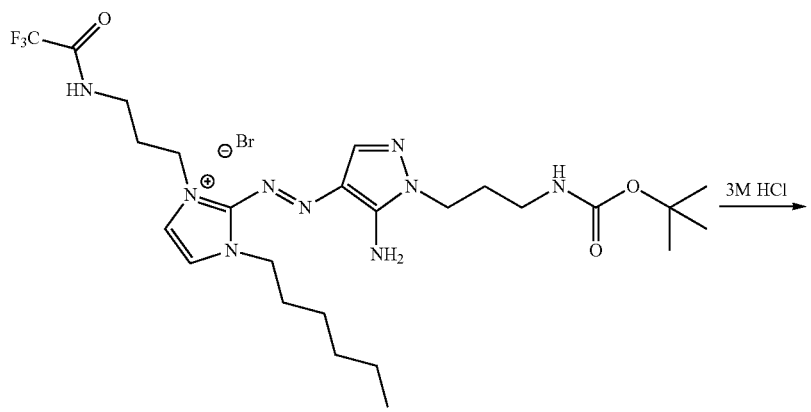

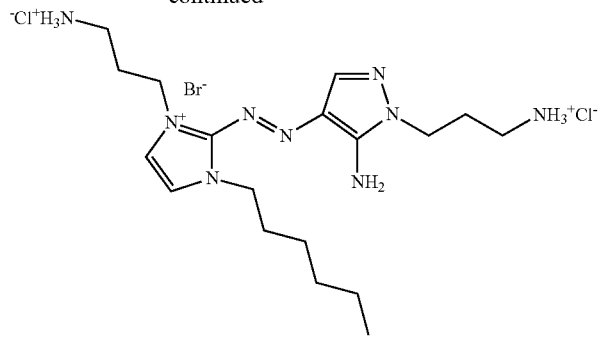

(E)-2-((5-amino-1-(3-((tert-butoxycarbonyl)amino)propyl)-1H-pyrazol-4-yl)diazenyl)-1-hexyl-3-(3-(2,2,2-trifluoroacetamido)propyl)-1H-imidazol-3-ium bromide (1.0 g, 1.53 mmol) is dissolved in 3M HCl (5 mL) and refluxed for 3 hours. The solvent is evaporated and the orange solid is re-dissolved in methanol and added to cold (−5° C.) ethyl acetate. The resulting precipitate is collected providing pure (E)-2-((5-amino-1-(3-ammoniopropyl)-1H-pyrazol-4-yl)diazenyl)-3-(3-ammoniopropyl)-1-hexyl-1H-imidazol-3-ium bromide dichloride (0.79 g, 1.50 mmol).

Example 8

In Example 8, (E)-3-(3-aminopropyl)-1-hexyl-2-((4,5,6,7-tetrahydropyrazolo[1,5-a]pyrimidin-3-yl)diazenyl)-1H-imidazol-3-ium bromide is prepared by cyclization of (E)-2-((5-amino-1-(3-ammoniopropyl)-1H-pyrazol-4-yl)diazenyl)-3-(3-ammoniopropyl)-1-hexyl-1H-imidazol-3-ium bromide dichloride in aqueous ammonium hydroxide.

(E)-3-(3-aminopropyl)-1-hexyl-2-((4,5,6,7-tetrahydropyrazolo[1,5-a]pyrimidin-3-yl)diazenyl)-1H-imidazol-3-ium bromide

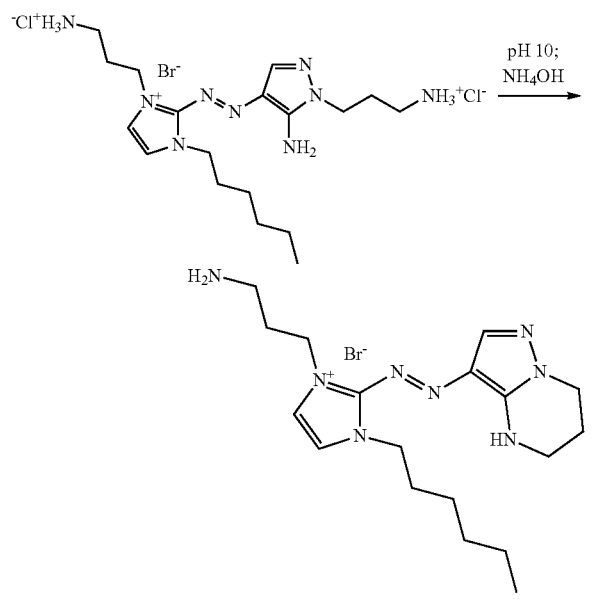

ium bromide dichloride is dissolved in aqueous ammonium hydroxide (2.25 g of 28% ammonium hydroxide and 97.75 g of water). After standing overnight, conversion to (E)-3-(3-aminopropyl)-1-hexyl-2-((4,5,6,7-tetrahydropyrazolo[1,5-a]pyrimidin-3-yl)diazenyl)-1H-imidazol-3-ium bromide is quantitative.

Example 9

In Example 9, (E)-2-((5-amino-1-(3-ammoniopropyl)-1H-pyrazol-4-yl)diazenyl)-1,3-bis(3-ammoniopropyl)-1H-imidazol-3-ium bromide trichloride is prepared from t-butyl (3-(5-amino-1H-pyrazol-1-yl)propyl)carbamate and 2-aminoimidazole.

Synthesis of t-butyl (E)-(3-(4-((1H-imidazol-2-yl)diazenyl)-5-amino-1H-pyrazol-1-yl)propyl)carbamate

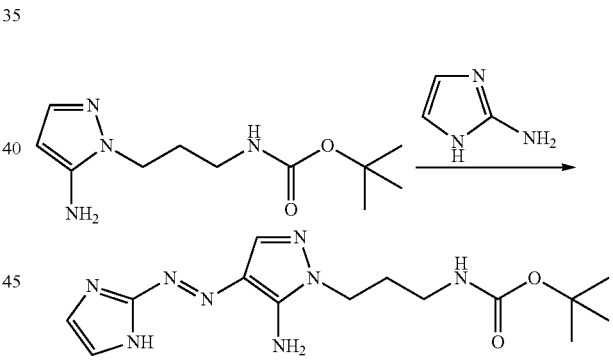

2-Aminoimidazole hemisulfate (10 g, 37.95 mmol) is dissolved in water (50 mL), concentrated HCl (25 g, 253 mmol) and the mixture cooled in ice/methanol bath to −5° C. Sodium nitrite (5.24 g, 76 mmol) is dissolved in a minimum amount of water and added dropwise, keeping the temperature below 0° C. The reaction mixture is allowed to stir for 30-60 minutes at <0° C. without allowing it to freeze. The t-butyl (3-(5-amino-1H-pyrazol-1-yl)propyl)carbamate (7.6 g, 31.63 mmol) is dissolved in methanol (50 mL) and water (200 mL). Sodium carbonate (33.4 g, 317 mmol) is added and the solution cooled in ice/water bath. The diazonium salt is added dropwise to this solution keeping the temperature around 5° C. The reaction mixture is allowed to warm to room temperature over 1 hour then extracted with 2×1 L of ethyl acetate. The ethyl acetate is evaporated and the residue chromatographed on silica gel, providing pure t-butyl (E)-(3-(4-((1H-imidazol-2-yl)diazenyl)-5-amino-1H-pyrazol-1-yl)propyl)carbamate (2.34 g, 5.6 mmol).

Synthesis of (E)-2-((5-amino-1-(3-((tert-butoxycarbonyl)amino)propyl)-1H-pyrazol-4-yl)diazenyl)-1,3-bis(3-(2,2,2-trifluoroacetamido)propyl)-1H-imidazol-3-ium bromide

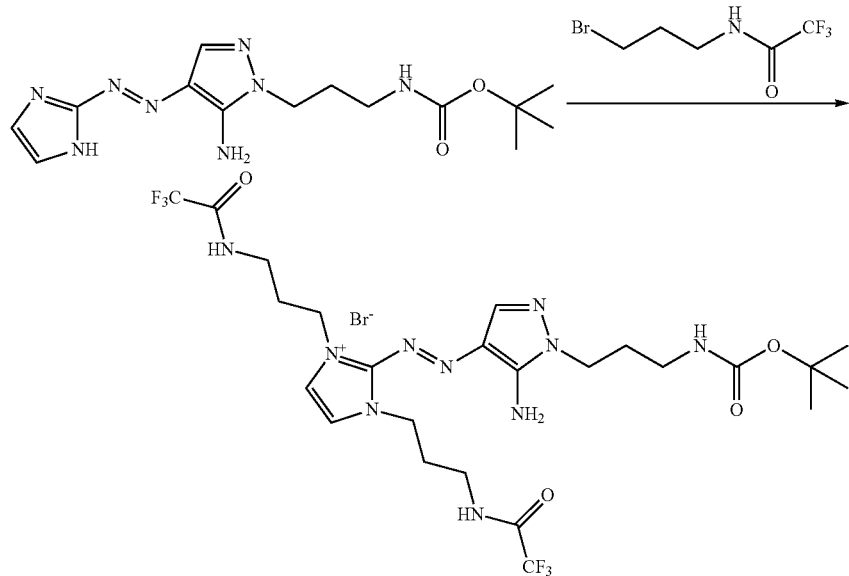

t-Butyl (E)-(3-(4-((1H-imidazol-2-yl)diazenyl)-5-amino-1H-pyrazol-1-yl)propyl)carbamate (0.40 g, 1.2 mmol) is suspended in acetonitrile (50 mL) and refluxed. N-(3-bromopropyl)-2,2,2-trifluoroacetamide (0.62 g, 2.63 mmol) and sodium bicarbonate (0.201 g, 2.40 mmol) were added and the reaction stirred at reflux overnight. The reaction mixture is filtered hot to remove sodium bicarbonate and the filtrate evaporated. The crude product is chromatographed on silica gel to afford pure (E)-2-((5-amino-1-(3-((tert-butoxycarbonyl)amino)propyl)-1H-pyrazol-4-yl)diazenyl)-1-hexyl-3-(3-(2,2,2-trifluoroacetamido)propyl)-1H-imidazol-3-ium bromide (0.70 g, 0.97 mmol).

Synthesis of (E)-2-((5-amino-1-(3-ammoniopropyl)-1H-pyrazol-4-yl)diazenyl)-1,3-bis(3-ammoniopropyl)-1H-imidazol-3-ium bromide trichloride

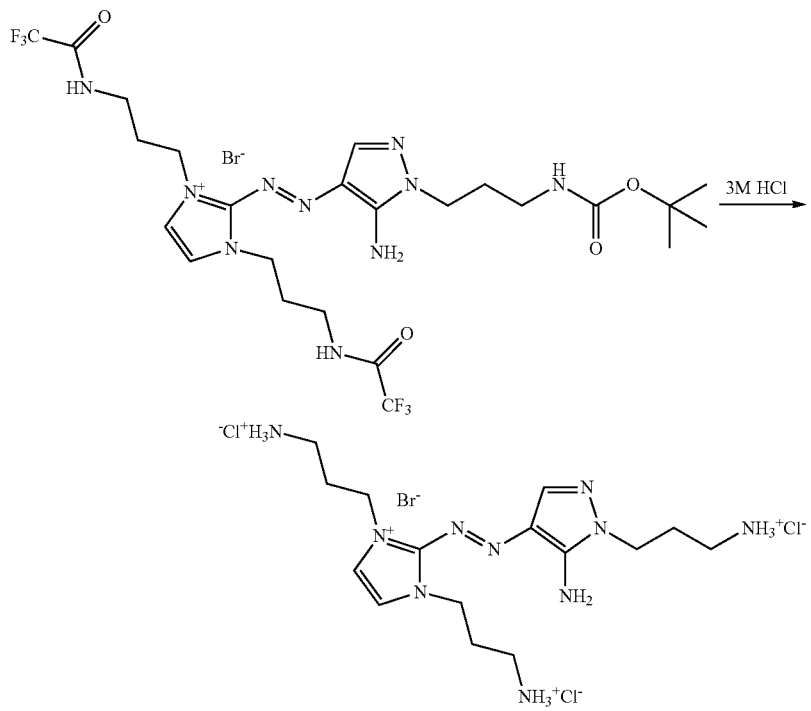

(E)-2-((5-amino-1-(3-((tert-butoxycarbonyl)amino)propyl)-1H-pyrazol-4-yl)diazenyl)-1,3-bis(3-(2,2,2-trifluoroacetamido)propyl)-1H-imidazol-3-ium bromide (0.70 g, 0.97 mmol) is dissolved in 3M HCl (5 mL) and refluxed for 3 hours. The solvent is evaporated, the solid re-dissolved in methanol and added to a cold (−5° C.) solution of ethyl acetate. The resulting precipitate is collected via filtration providing pure (E)-2-((5-amino-1-(3-ammoniopropyl)-1H-pyrazol-4-yl)diazenyl)-1,3-bis(3-ammoniopropyl)-1H-imidazol-3-ium bromide trichloride (0.52 g, 0.968 mmol).

Example 10

In Example 10, (E)-1,3-bis(3-aminopropyl)-2-((4,5,6,7-tetrahydropyrazolo[1,5-a]pyrimidin-3-yl)diazenyl)-1H-imidazol-3-ium bromide is prepared by cyclization (E)-2-((5-amino-1-(3-ammoniopropyl)-1H-pyrazol-4-yl)diazenyl)-1,3-bis(3-ammoniopropyl)-1H-imidazol-3-ium bromide trichloride.

(E)-1,3-bis(3-aminopropyl)-2-((4,5,6,7-tetrahydropyrazolo[1,5-a]pyrimidin-3-yl)diazenyl)-1H-imidazol-3-ium bromide

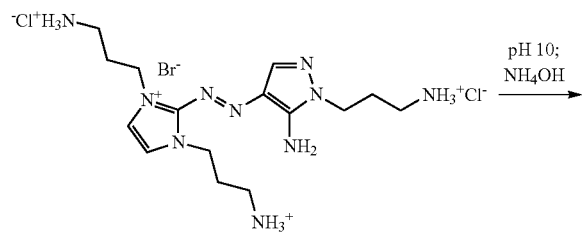

(E)-2-((5-amino-1-(3-ammoniopropyl)-1H-pyrazol-4-yl)diazenyl)-1,3-bis(3-ammoniopropyl)-1H-imidazol-3-ium bromide trichloride is dissolved in aqueous ammonium hydroxide (2.25 g of 28% ammonium hydroxide and 97.75 g of water). After standing overnight, conversion to (E)-1,3-bis(3-aminopropyl)-2-((4,5,6,7-tetrahydropyrazolo[1,5-a]pyrimidin-3-yl)diazenyl)-1H-imidazol-3-ium bromide is quantitative.

Example 11

In Example 11, (E)-2-((5-amino-1-(3-ammoniopropyl)-1H-pyrazol-4-yl)diazenyl)-3-(3-ammoniopropyl)-1-propyl-1H-imidazol-3-ium bromide dichloride is prepared from (E)-N'-(1H-imidazol-2-yl)-N,N-dimethylformimidamide and t-butyl (3-(5-amino-1H-pyrazol-1-yl)propyl)carbamate Synthesis of (E)-N,N-dimethyl-N'-(1-propyl-1H-imidazol-2-yl)formimidamide

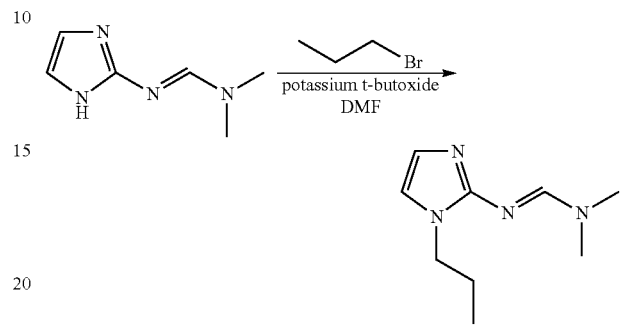

(E)-N'-(1H-imidazol-2-yl)-N,N-dimethylformimidamide (4.82 g, 34.63 mmol) is dissolved in dimethylformamide (100 mL). Potassium t-butoxide (8.55 g, 76.2 mmol) is added followed by 1-bromopropane (6.39 g, 51.95 mmol) and the mixture stirred at 40° C. overnight. The reaction mixture is then quenched with water (50 mL), followed by acidification with concentrated HCl and extraction with dichloromethane. The combined dichloromethane extracts were washed with water (3×100 mL) dried (MgSO$_4$), filtered, and evaporated affording very pure (E)-N'-(1-propyl-1H-imidazol-2-yl)-N,N-dimethylformimidamide (6.0 g, 96%).

Synthesis of 1-propyl-1H-imidazol-2-aminium chloride

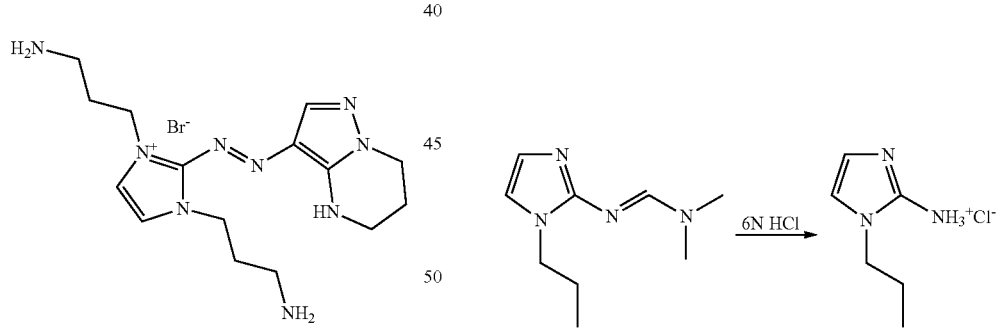

(E)-N'-(1-propyl-1H-imidazol-2-yl)-N,N-dimethylformimidamide (6.24 g, 34.6 mmol) is suspended in 6N HCl (50 mL) and refluxed for 3 hours. After most of the water is removed the solution is re-dissolved in 1N NaOH and this solution evaporated to remove the possible dimethylamine impurity. Following complete evaporations the crude product is dissolved in 1N HCl and the solvent is evaporated. The dry solid is triturated with ethyl ether. The suspended solids were collected via filtration affording 1-propyl-1H-imidazol-2-aminium chloride (5.3 g, 40.7 mmol) as a crude, off-white solid.

Synthesis of tert-butyl (E)-(3-(5-amino-4-((1-hexyl-1H-imidazol-2-yl)diazenyl)-1H-pyrazol-1-yl)propyl)carbamate

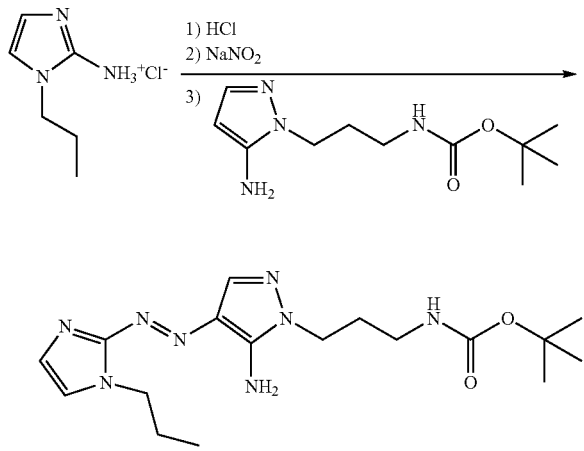

1-Propyl-1H-imidazol-2-aminium chloride (1.0 g, 6.2 mmol) is dissolved in water (20 mL), concentrated HCl (2.69 g, 27.22 mmol) is added and the mixture cooled in ice/methanol bath to −5° C. Sodium nitrite (0.57 g, 6.81 mmol) is dissolved in a minimum amount of water and added dropwise to the above mixture keeping the temperature below 0° C. The reaction mixture is allowed to stir for 30-60 minutes at <0° C. without allowing it to freeze. The t-butyl (3-(5-amino-1H-pyrazol-1-yl)propyl)carbamate (1.635 g, 6.81 mmol) is dissolved the minimum amount of methanol (5 mL) and water added to the cloud point. This solution is added to the above diazonium salt keeping the temperature around 5° C. After 15-30 minutes there is a heavy black precipitate in the reaction. While stirring the mixture, 50% NaOH is added dropwise until the mixture is ca. pH 10.0. The resulting mixture is extracted several times with 200 mL ethyl acetate. The combined ethyl acetate extracts were evaporated and the residue chromatographed on silica gel providing pure t-butyl (E)-(3-(5-amino-4-((1-propyl-1H-imidazol-2-yl)diazenyl)-1H-pyrazol-1-yl)propyl)carbamate (1.05 g, 2.8 mmol).

Synthesis of (E)-2-((5-amino-1-(3-((tert-butoxycarbonyl)amino)propyl)-1H-pyrazol-4-yl)diazenyl)-1-propyl-3-(3-(2,2,2-trifluoroacetamido)propyl)-1H-imidazol-3-ium bromide

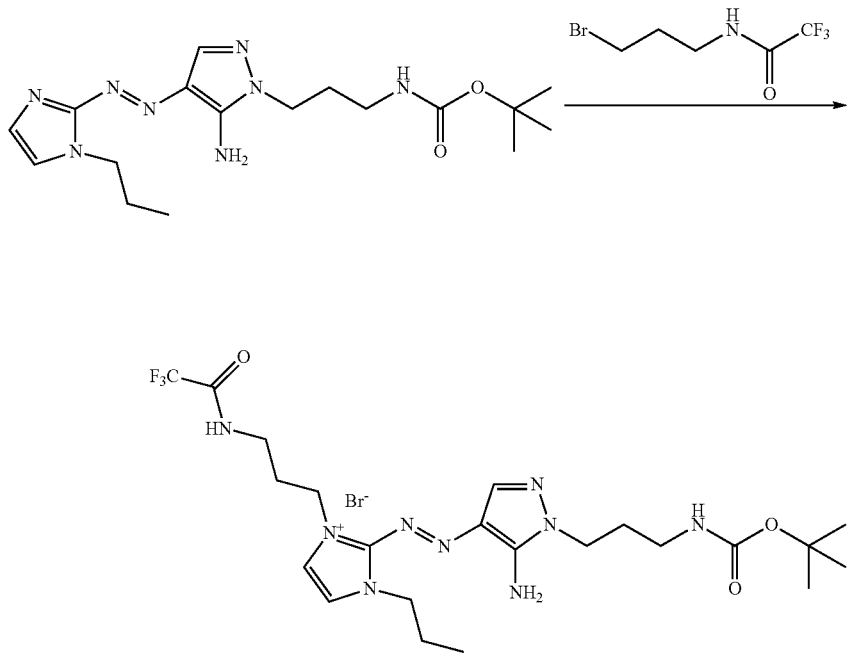

t-Butyl (E)-(3-(5-amino-4-((1-propyl-1H-imidazol-2-yl)diazenyl)-1H-pyrazol-1-yl)propyl)carbamate (1.05 g, 2.8 mmol) is suspended in acetonitrile (50 mL) and N-(3-bromopropyl)-2,2,2-trifluoroacetamide (1.44 g, 6.14 mmol) is added and the mixture refluxed overnight. Additional N-(3-bromopropyl)-2,2,2-trifluoroacetamide (0.700 g, 2.99 mmol) is added and the mixture is refluxed overnight. The solvent is evaporated and the crude product is chromatographed on silica gel to afford pure (E)-2-((5-amino-1-(3-((tert-butoxycarbonyl)amino)propyl)-1H-pyrazol-4-yl)diazenyl)-1-propyl-3-(3-(2,2,2-trifluoroacetamido)propyl)-1H-imidazol-3-ium bromide (1.0 g, 1.53 mmol).

Synthesis of (E)-2-((5-amino-1-(3-ammoniopropyl)-1H-pyrazol-4-yl)diazenyl)-3-(3-ammoniopropyl)-1-propyl-1H-imidazol-3-ium bromide dichloride

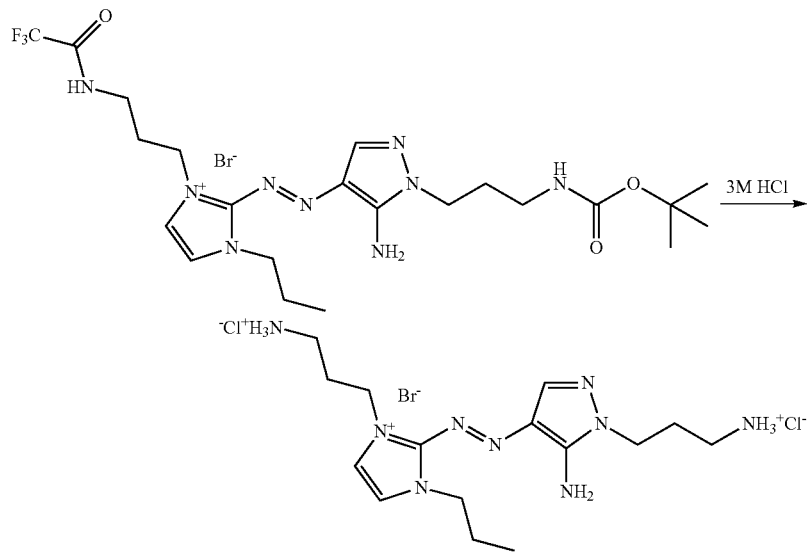

(E)-2-((5-amino-1-(3-((tert-butoxycarbonyl)amino)propyl)-1H-pyrazol-4-yl)diazenyl)-1-propyl-3-(3-(2,2,2-trifluoroacetamido)propyl)-1H-imidazol-3-ium bromide (1.0 g, 1.53 mmol) is dissolved in 3M HCl (5 mL) and refluxed for 3 hours. The solvent is evaporated and the orange solid is re-dissolved in methanol and added to a cold (−5° C.) solution of ethyl acetate. The resulting precipitate is collected via filtration providing pure (E)-2-((5-amino-1-(3-ammoniopropyl)-1H-pyrazol-4-yl)diazenyl)-3-(3-ammoniopropyl)-1-propyl-1H-imidazol-3-ium bromide dichloride (0.70 g, 1.43 mmol).

Example 12

In Example 12, (E)-3-(3-aminopropyl)-1-propyl-2-((4,5,6,7-tetrahydropyrazolo[1,5-a]pyrimidin-3-yl)diazenyl)-1H-imidazol-3-ium bromide is prepared by cyclization (E)-2-((5-amino-1-(3-ammoniopropyl)-1H-pyrazol-4-yl)diazenyl)-1,3-bis(3-ammoniopropyl)-1H-imidazol-3-ium bromide trichloride.

(E)-3-(3-aminopropyl)-1-propyl-2-((4,5,6,7-tetrahydropyrazolo[1,5-a]pyrimidin-3-yl)diazenyl)-1H-imidazol-3-ium bromide

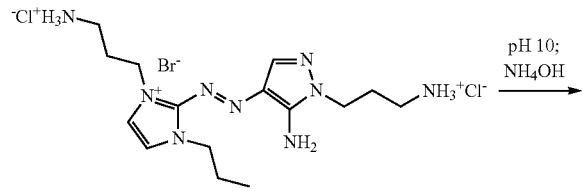

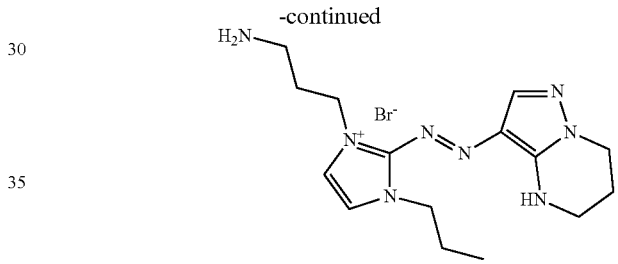

(E)-2-((5-amino-1-(3-ammoniopropyl)-1H-pyrazol-4-yl)diazenyl)-1,3-bis(3-ammoniopropyl)-1H-imidazol-3-ium bromide trichloride is dissolved in aqueous ammonium hydroxide (2.25 g of 28% ammonium hydroxide and 97.75 g of water). After standing overnight, conversion to (E)-3-(3-aminopropyl)-1-propyl-2-((4,5,6,7-tetrahydropyrazolo[1,5-a]pyrimidin-3-yl)diazenyl)-1H-imidazol-3-ium bromide is quantitative.

Example 13

In Example 13, (E)-2-((5-amino-1-propyl-1H-pyrazol-4-yl)diazenyl)-1,3-bis(3-ammoniopropyl)-1H-imidazol-3-ium bromide dichloride is prepared from acrylonitrile and 2-aminoimidazole.

Synthesis of 3-hydrazinylpropanitrile

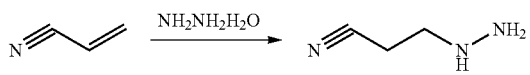

64-65% Hydrazine hydrate (1:1) (11.2 g, 0.224 mol) is dissolved in 1-propanol (200 mL) and cooled in ice-methanol to −5° C. Acrylonitrile (12.47 g, 0.235 mol) is added dropwise keeping the internal temperature below 0° C. The reaction is stirred at −5° C. for 30 minutes and then allowed to warm to room temperature and stirred for 1 hour. This material, 3-hydrazinylpropanitrile, is used directly in the next reaction.

Synthesis of (E)-3-(2-propylidenehydrazinyl)propanenitrile

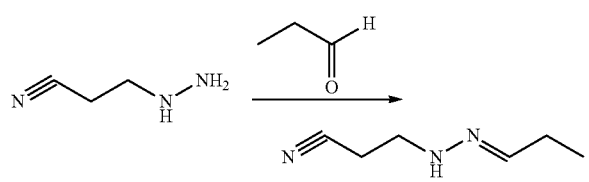

1-Propionaldehyde (6.8 g, 117 mmol) is added dropwise at room temperature to a portion of the freshly prepared 3-hydrazinylpropanitrile solution (theoretical 6.125 g, 72 mmol) above, keeping the internal temperature below 30° C. The solution is stirred for 1 hour at room temperature followed by solvent evaporation providing (E)-3-(2-propylidenehydrazinyl)-propanenitrile.

Synthesis of 1-propyl-1H-pyrazol-5-amine

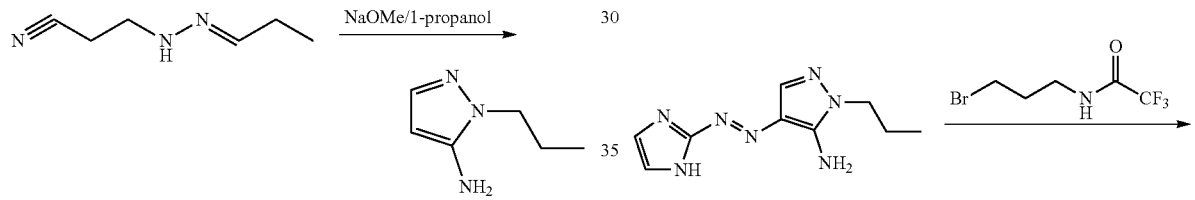

(E)-3-(2-propylidenehydrazinyl)propanenitrile (9.0 g, 71.88 mmol) is added to a 250 mL round bottom flask along with 100 mL 1-propanol. Sodium methoxide, 25% (1.55 g, 7.18 mmol) is added and the mixture heated to reflux for 3 hours after which additional sodium methoxide (1.5 g) is added and reflux continued over the weekend. The 1-propanol is evaporated and the residue chromatographed on silica gel to afford 1-propyl-1H-pyrazol-5-amine (4.0 g, 32 mmol).

Synthesis of (E)-4-((1H-imidazol-2-yl)diazenyl)-1-propyl-1H-pyrazol-5-amine

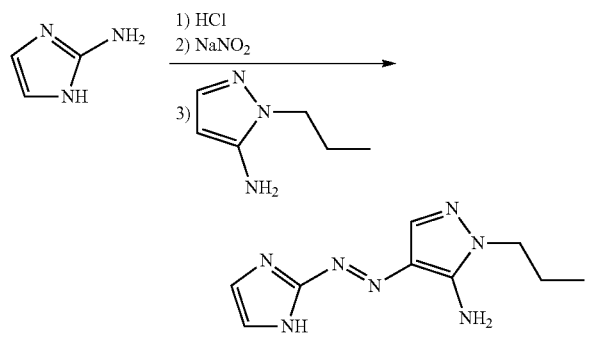

2-Aminoimidazole (5.99 g, 22.7 mmol) is dissolved in water (50 mL) followed by the addition of concentrated hydrochloric acid (8.94 g, 90.67 mmol) and acetic acid (2.72 g, 45.33 mmol). This mixture is cooled in an ice-methanol bath to −5° C. Sodium nitrite (3.13 g, 45.33 mmol) is dissolved in a minimum amount of water (<4 mL) and added slowly to the 2-amino-imidazole keeping temperature below 0° C. This diazonium salt is maintained at <0° C.

In a separate flask, 1-propyl-1H-pyrazol-5-amine (4 g, 41.21 mmol) is dissolved in a minimum amount of ethanol and water is added to the cloud point. This solution is added to the diazonium salt above keeping temperature below 5° C. After 15-30 minutes at <5° C. the resulting black heterogeneous solution is made basic via the addition of 50% NaOH. NaOH is added while stirring. The resulting solution is extracted several times with ethyl acetate. The ethyl acetate is evaporated. The crude product is chromatographed on silica gel affording pure (E)-4-((1H-imidazol-2-yl)diazenyl)-1-propyl-1H-pyrazol-5-amine (3.1 g, 14.1 mmol).

Synthesis of (E)-2-((5-amino-1-propyl-1H-pyrazol-4-yl)diazenyl)-1,3-bis(3-(2,2,2-trifluoroacetamido)propyl)-1H-imidizol-3-ium bromide

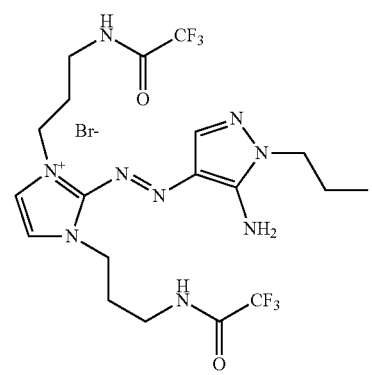

(E)-4-((1H-imidazol-2-yl)diazenyl)-1-propyl-1H-pyrazol-5-amine (2.0 g, 9.12 mmol) is dissolved in 100 mL of acetonitrile. Sodium bicarbonate (1.68 g, 27.4 mmol) and 3-bromopropyl trifluoroacetamide (6.4 g, 27.4 mmol) were added and the reaction heated to reflux overnight. The reaction is filtered hot to remove sodium bicarbonate and the solvent evaporated. The resulting residue is chromatographed on silica gel affording (E)-2-((5-amino-1-propyl-1H-pyrazol-4-yl)diazenyl)-1,3-bis(3-(2,2,2-trifluoroacetamido)propyl)-1H-imidizol-3-ium bromide (4.1 g, 6.77 mmol).

Synthesis of (E)-2-((5-amino-1-propyl-1H-pyrazol-4-yl)diazenyl)-1,3-bis(3-aminopropyl)-1H-imidizol-3-ium bromide dihydrochloride

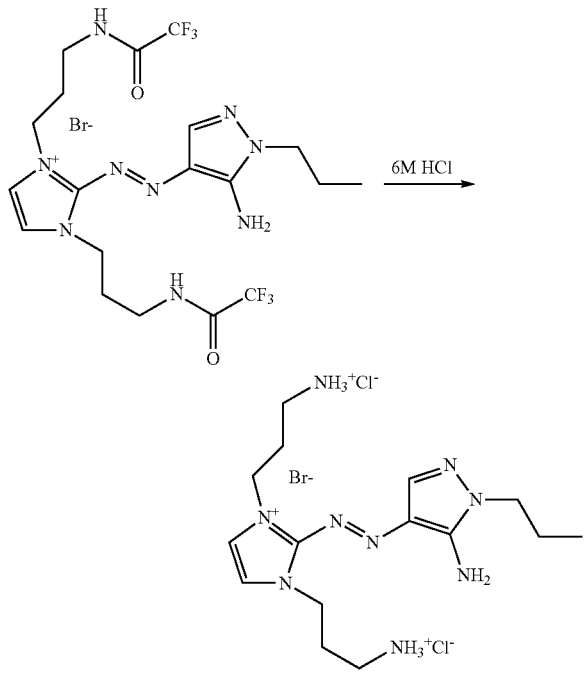

Synthesis of (E)-3-(2-propylidenehydrazinyl)propanenitrile

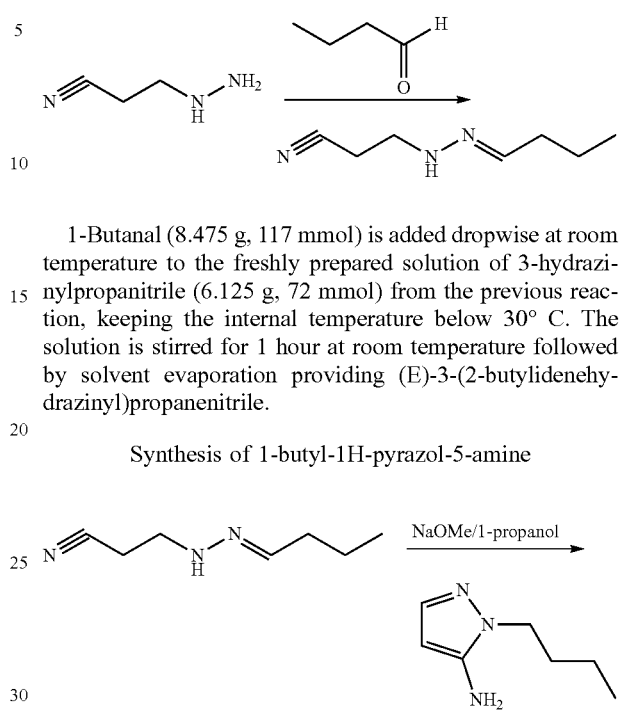

1-Butanal (8.475 g, 117 mmol) is added dropwise at room temperature to the freshly prepared solution of 3-hydrazinylpropanitrile (6.125 g, 72 mmol) from the previous reaction, keeping the internal temperature below 30° C. The solution is stirred for 1 hour at room temperature followed by solvent evaporation providing (E)-3-(2-butylidenehydrazinyl)propanenitrile.

Synthesis of 1-butyl-1H-pyrazol-5-amine

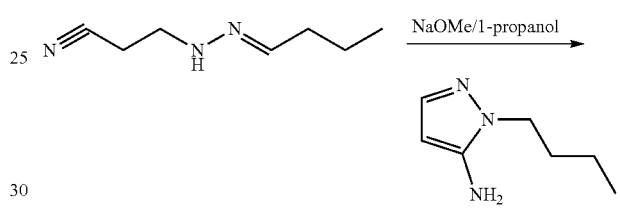

(E)-2-((5-amino-1-propyl-1H-pyrazol-4-yl)diazenyl)-1,3-bis(3-(2,2,2-trifluoroacetamido)-propyl)-1H-imidizol-3-ium bromide (2.0 g, 30.1 mmol) is suspended in 25 mL (0.9 mol) of concentrated HCl and refluxed for 2 hours. The hydrochloric acid is evaporated and the product dissolved in a minimum of methanol followed by addition to cold (−5° C.) ethyl acetate (150 mL). This suspension is subsequently filtered under inert atmosphere to afford pure (E)-2-((5-amino-1-propyl-1H-pyrazol-4-yl)diazenyl)-1,3-bis(3-aminopropyl)-1H-imidizol-3-ium bromide dihydrochloride (1.38 g, 2.83 mmol).

(E)-3-(2-butylidenehydrazinyl)propanenitrile (10 g, 72 mmol) is added to a 250 mL round bottom flask along with 100 mL 1-propanol. Sodium methoxide, 25% (5.0 g, 23 mmol) is added and the mixture heated to reflux for 48 hours after which the solvent is evaporated and chromatographed on silica gel afford pure 1-butyl-1H-pyrazol-5-amine (4.3 g, 31 mmol).

Synthesis of (E)-4-((1H-imidazol-2-yl)diazenyl)-1-butyl-1H-pyrazol-5-amine

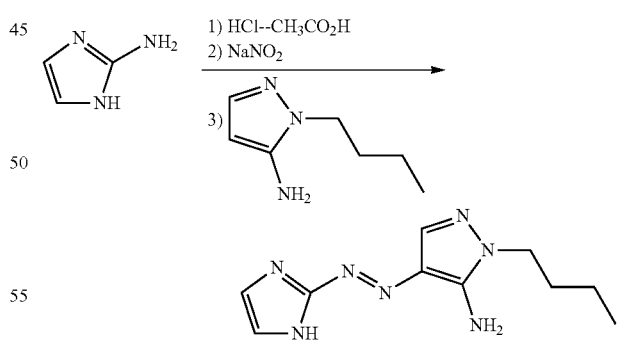

Example 14

In Example 14, (E)-2-((5-amino-1-butyl-1H-pyrazol-4-yl)diazenyl)-1,3-bis(3-aminopropyl)-1H-imidizol-3-ium bromide dihydrochloride is prepared from 2-aminoimidazole and acrylonitrile.

Synthesis of 3-hydrazinylpropanitrile

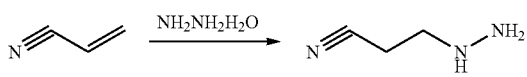

64-65% Hydrazine hydrate (1:1) (11.2 g, 0.224 mol) is dissolved in 1-propanol (200 mL) and cooled in ice-methanol to −5° C. Acrylonitrile (12.47 g, 0.235 mol) is added dropwise keeping the internal temperature below 0° C. The reaction is stirred at −5° C. for 30 minutes, and then warmed to room temperature and stirred for 1 hour. This material, 3-hydrazinylpropanitrile, is used directly in the next reaction.

2-Aminoimidazole (1.14 g, 4.35 mmol) is dissolved in water (20 mL) followed by the addition of concentrated hydrochloric acid (3.12 g, 31.6 mmol) and acetic acid (0.522 g, 8.69 mmol). This mixture is cooled in an ice-methanol bath to −5° C. Sodium nitrite (0.60 g, 8.69 mmol) is dissolved in a minimum amount of water (<2 mL) and added slowly to the 2-aminoimidazole containing solution, keeping temperature below 0° C. The diazonium salt and it is maintained at <0° C.

In a separate flask, 1-butyl-1H-pyrazol-5-amine (1.1 g, 7.9 mmol) is dissolved in a minimum amount of ethanol, and water is added to the cloud point. This solution is added to the diazonium salt above, keeping temperature below 5° C. After 15-30 minutes at <5° C. the resulting black heterogeneous solution is made basic via the addition of 50% NaOH, with stirring. The solution is extracted several times with ethyl acetate. The ethyl acetate extracts are combined and evaporated. The crude product is chromatographed on silica gel affording pure (E)-4-((1H-imidazol-2-yl)diazenyl)-1-butyl-1H-pyrazol-5-amine (0.750 g, 3.44 mmol).

Synthesis of (E)-2-((5-amino-1-butyl-1H-pyrazol-4-yl)diazenyl)-1,3-bis(3-(2,2,2-trifluoroacetamido)propyl)-1H-imidizol-3-ium bromide

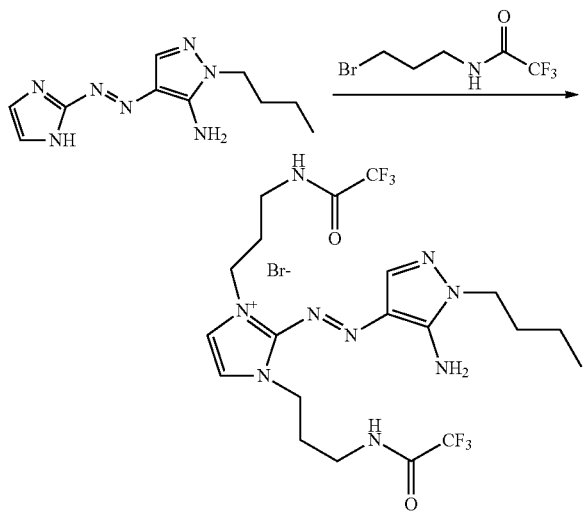

(E)-4-((1H-imidazol-2-yl)diazenyl)-1-butyl-1H-pyrazol-5-amine (0.750 g, 3.44 mmol) is dissolved in 30 mL of acetonitrile. Sodium bicarbonate (0.54 g, 6.43 mmol) and 3-bromopropyl trifluoroacetamide (2.26 g, 9.65 mmol) were added and the reaction is heated to reflux overnight. The reaction is filtered hot to remove sodium bicarbonate and the solvent is evaporated. The resulting residue is chromatographed on silica gel affording (E)-2-((5-amino-1-butyl-1H-pyrazol-4-yl)diazenyl)-1,3-bis(3-(2,2,2-trifluoroacetamido)propyl)-1H-imidizol-3-ium bromide (0.88 g, 1.45 mmol).

Synthesis of (E)-2-((5-amino-1-butyl-1H-pyrazol-4-yl)diazenyl)-1,3-bis(3-aminopropyl)-1H-imidizol-3-ium bromide dihydrochloride

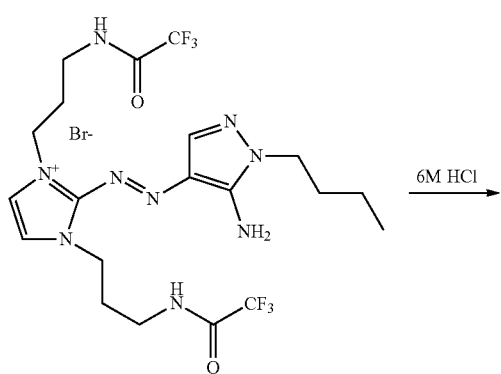

(E)-2-((5-amino-1-butyl-1H-pyrazol-4-yl)diazenyl)-1,3-bis(3-(2,2,2-trifluoroacetamido)propyl)-1H-imidizol-3-ium bromide (0.88 g, 1.45 mmol) is suspended in 10 mL of concentrated HCl and refluxed for 2 hours. The hydrochloric acid is evaporated and the product dissolved in a minimum of methanol followed by addition to cold (−5° C.) ethyl acetate (100 mL). This suspension is filtered under inert atmosphere and affords pure (E)-2-((5-amino-1-butyl-1H-pyrazol-4-yl)diazenyl)-1,3-bis(3-aminopropyl)-1H-imidizol-3-ium bromide dihydrochloride (0.67 g, 1.37 mmol).

Example 15

In example 15, (E)-2-((5-amino-1-methyl-1H-pyrazol-4-yl)diazenyl)-1,3-dimethyl-1H-imidazol-3-ium methyl sulfate is prepared from 2-aminoimidazole and 1-Methyl-1H-pyrazol-5-amine.

Synthesis of (E)-2-((5-amino-1-methyl-1H-pyrazol-4-yl)diazenyl)-1,3-dimethyl-1H-imidazol-3-ium

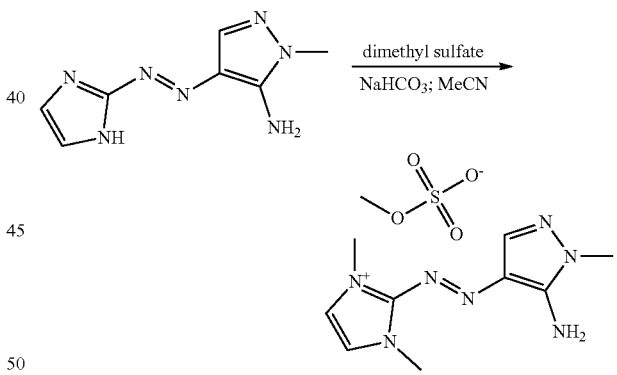

A solution of 191 mg of crude (E)-4-((1H-imidazol-2-yl)diazenyl)-1-methyl-1H-pyrazol-5-amine, 504 mg of NaHCO₃, and 568 mg of dimethyl sulfate in 10 mL of acetonitrile is heated under reflux for 4 hours. The reaction mixture is filtered hot, and the filtrate is evaporated to dryness. The residue is dissolved in a minimum amount of methanol, the solution is poured into cold ethyl acetate, and the precipitate is collected, yielding 66 mg of (E)-2-((5-amino-1-methyl-1H-pyrazol-4-yl)diazenyl)-1,3-dimethyl-1H-imidazol-3-ium methyl sulfate as a yellowish solid.

Example 16

In example 16, Yellow Polyethyleneimine Polymer is prepared from (E)-N-(1H-imidazol-2-yl)-N,N-dimethylformimidamide and polyethyleneimine.

Synthesis of (E)-2-((5-amino-1-hexyl-1H-pyrazol-4-yl)diazenyl)-1-(3-bromopropyl)-3-methyl-1H-imidazol-3-ium bromide (E)-1-hexyl-4-((1-methyl-1H-imidazol-2-yl)diazenyl)-1H-pyrazol-5-amine

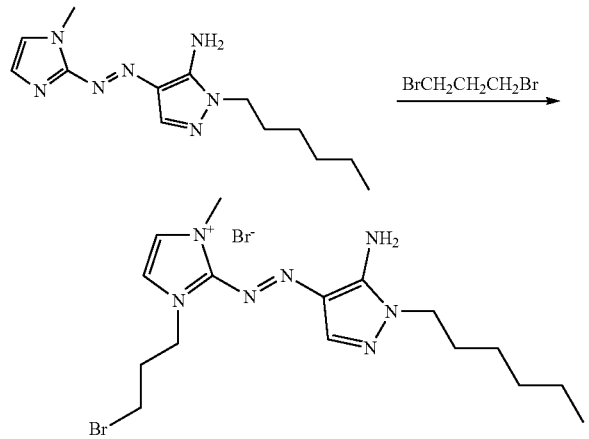

(E)-1-hexyl-4-((1-methyl-1H-imidazol-2-yl)diazenyl)-1H-pyrazol-5-amine (0.19 g, 0.69 mmol) is dissolved in acetonitrile (50 mL). 1,3-Dibromopropane (1.39 g) is added and the mixture is refluxed overnight. The solution is evaporated and the residue chromatographed on silica gel, providing (E)-2-((5-amino-1-hexyl-1H-pyrazol-4-yl)diazenyl)-3-(3-bromopropyl)-1-methyl-1H-imidazol-3-ium bromide (0.05 g).

Synthesis of Yellow Polyethyleneimine Polymer

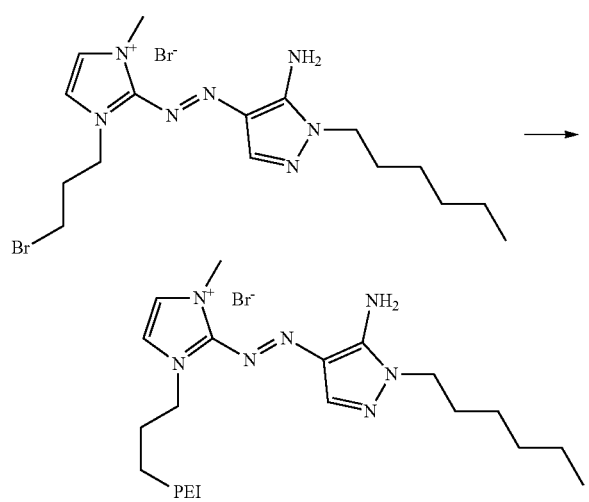

(E)-2-((5-amino-1-hexyl-1H-pyrazol-4-yl)diazenyl)-1-(3-bromopropyl)-3-methyl-1H-imidazol-3-ium bromide (0.05 g) is dissolved in acetonitrile. Polyethyleneimine, (46 mg) is added and the mixture heated to reflux. After completion the solution is evaporated and triturated with dichloromethane. The remaining solid is placed on high vacuum providing the yellow polyethyleneimine dye.

Exemplary Formulations

| | % by weight |
|---|---|
| Composition A | |
| Stable Direct Yellow Dye[1] | 0.01-2.5 |
| Ammonium Hydroxide (aq. 28% active) | 4.50 |
| Water | q.s. to 100 |
| Composition B | |
| Stable Direct Yellow Dye[1] | 0.01-2.5 |
| Ammonium carbonate | 10.00 |
| Water | q.s. to 100 |
| Composition C | |
| Stable Direct Yellow Dye[1] | 0.01-2.5 |
| FlexiThix ™[3] | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition D | |
| Stable Direct Yellow Dye[1] | 0.01-2.5 |
| Aculyn ™ 46[4] | 15.80 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition E | |
| Stable Direct Yellow Dye[1] | 0.01-2.5 |
| Plantaren ® 2000 N UP[2] | 20.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition F | |
| Stable Direct Yellow Dye[1] | 0.01-2.5 |
| Non-anionic foaming agent | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |

[1]The stable direct yellow dye may be any one of the direct yellow dyes described herein
[2]Chemical makeup supplied by BASF
[3]PVP polymer supplied by Ashland
[4]PEG-150/Stearyl/SMDI copolymer supplied by Rohm and Haas Data In-Use Disappearance Disappearance of the dye is measured on a Cary 100 UV/visible spectrophotometer at 25° C. A solution of the dye in water at a concentration sufficient to give an absorbance of 2.0 at the dye's λmax and buffered at pH 10.6 with ammonia is mixed with an equal volume of 6% hydrogen peroxide in a 1 cm quartz cuvette. The absorbance is measured at the λmax at zero ($A_0$) and thirty minutes ($A_{30}$) reaction time. Percent disappearance is calculated as the difference between the starting and thirty-minute absorbances divided by the starting absorbance minus the baseline absorbance ($A_b$), by the following equation:

$$\% \text{ Disappearance} = \frac{(A_0 - A_{30})}{(A_0 - A_b)} \times 100$$

Results are reported in Table 2 below.

Color Intensity

The exemplary formulations indicated above are formulated with yellow imidazolium azo dyes. These are applied directly to fabric test cloth, and then rinsed with water after thirty minutes. The resulting color is measured using a colorimeter with D65 illumination and characterized by the L* value. An L* of 100 is considered white and L* of 0 is considered black, therefore the higher the L* value the lower the color intensity. The measured L* values for different compounds of the present invention are summarized in Table 1 below.

TABLE 1

Colorstrike on natural white hair from imidazolium azo dyes in water adjusted to pH 10.8 with 28% ammonia, and then mixed with an equal volume of Clairol Professional ® Soy 4Plex Clairoxide ®.

| Example Number | Structure | L | a | b | C | h |
|---|---|---|---|---|---|---|
| 1 | [structure] | 64.93 | 20.79 | 77.82 | 80.56 | 75.05 |
| 2 | [structure] | 67.47 | 21.46 | 80.96 | 83.76 | 75.15 |
| 3 | [structure] | 67.58 | 19.74 | 82.22 | 84.56 | 76.50 |
| 4 | [structure] | 67.68 | 20.97 | 81.94 | 84.58 | 75.65 |

TABLE 1-continued

Colorstrike on natural white hair from imidazolium azo dyes in water adjusted to pH 10.8 with 28% ammonia, and then mixed with an equal volume of Clairol Professional ® Soy 4Plex Clairoxide ®.

| Example Number | Structure | L | a | b | C | h |
|---|---|---|---|---|---|---|
| 5 | 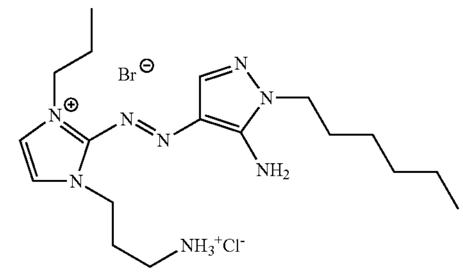 | 66.76 | 23.99 | 81.12 | 84.60 | 73.52 |
| 6 | 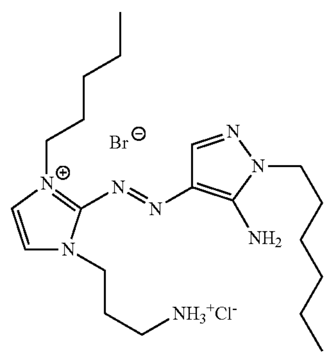 | 65.19 | 26.22 | 77.70 | 82.01 | 71.35 |
| 7 | 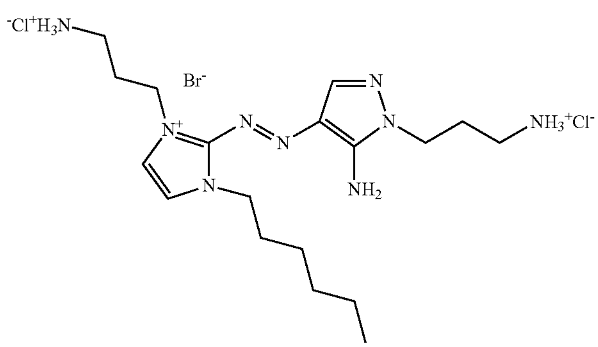 | 66.75 | 21.80 | 79.72 | 82.65 | 74.71 |
| 9 | 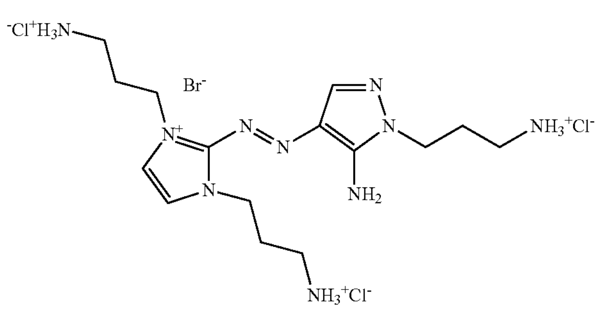 | 68.42 | 19.47 | 80.96 | 83.27 | 76.49 |
| 11 | 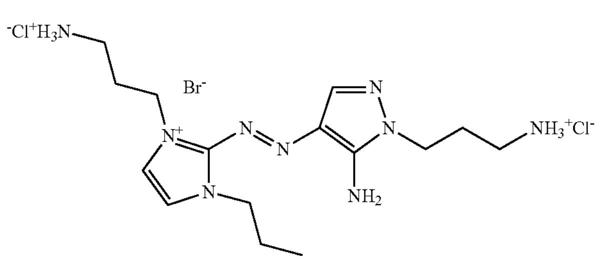 | 67.64 | 22.16 | 82.41 | 85.34 | 74.95 |

TABLE 1-continued
Colorstrike on natural white hair from imidazolium azo dyes in water adjusted to pH 10.8 with 28% ammonia, and then mixed with an equal volume of Clairol Professional ® Soy 4Plex Clairoxide ®.
| Example Number | Structure | L | a | b | C | h |
|---|---|---|---|---|---|---|
| 12 | 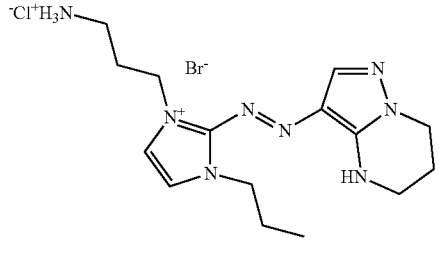 | 66.11 | 30.38 | 78.2 | 83.89 | 68.77 |
| 13 | 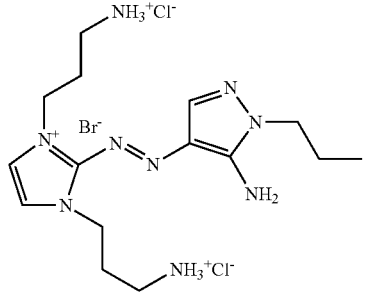 | 68.57 | 24.20 | 83.43 | 86.87 | 73.82 |
| 14 | 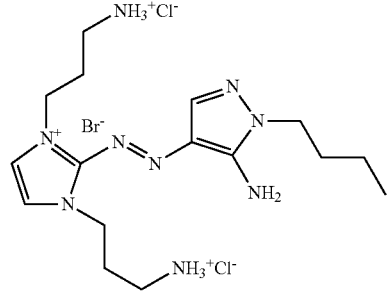 | 67.38 | 24.85 | 81.25 | 84.97 | 73.00 |
| 15 | 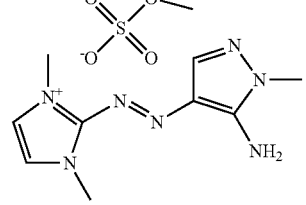 | 69.82 | 19.95 | 86.94 | 89.21 | 77.09 |

TABLE 2

Color and in-use stability for example dyes.

| Example Number | Structure | Color ($\lambda$max; nm) | % Disappearance (In-use) |
|---|---|---|---|
| 1 | [structure] | 437 | 0 |
| 2 | [structure] | 438 | 0 |
| 3 | [structure] | 436 | 0 |
| 4 | [structure] | 436 | 1.28 |
| 5 | [structure] | 436 | 0 |

TABLE 2-continued
Color and in-use stability for example dyes.
| Example Number | Structure | Color (λmax; nm) | % Disappearance (In-use) |
|---|---|---|---|
| 6 | 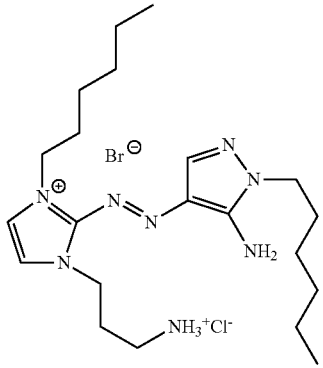 | 436 | 0 |
| 7 | 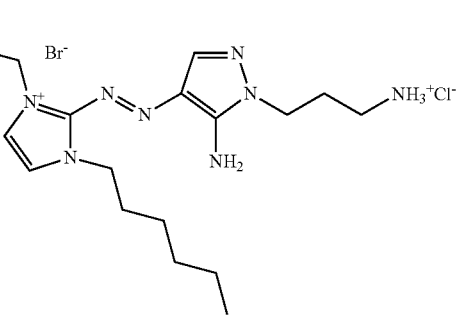 | 436 | 5.7 |
| 8 | 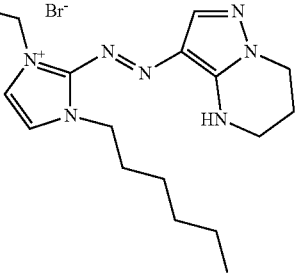 | 446 | 2.79 |
| 10 | 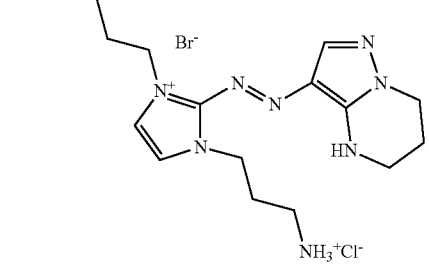 | 448 | 2.78 |

TABLE 2-continued

Color and in-use stability for example dyes.

| Example Number | Structure | Color (λmax; nm) | % Disappearance (In-use) |
|---|---|---|---|
| 12 | [structure] | 448 | 3.55 |
| 13 | [structure] | 437 | 0 |
| 14 | [structure] | 436 | 0 |
| 15 | [structure] | 433 | 0 |

* % loss recorded at 30 minutes in the presence of a 3% $H_2O_2$ solution at pH10.6.

It is noted that terms like "preferably," "usually", "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention may be identified herein as preferred or particularly advantageous, it is contemplated that the present invention is not necessarily limited to these preferred aspects of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound having a structure according to Formula V and tautomers and salts thereof:

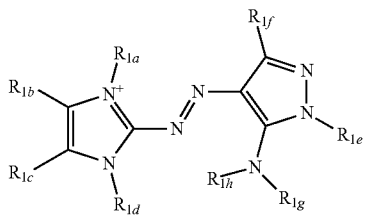

Formula (V)

wherein:
(i) $R_{1b}$, $R_{1c}$ and $R_{1f}$ are independently selected from the group consisting of hydrogen, alkyl, halogen substituted alkyl, alkenyl, alkynyl, aryl, hydroxyalkyl, aminoalkyl, alkyl group carrying a quaternary ammonium cation, alkoxy, aryloxy, acyl, halogen, a heterocyclic moiety, thioether, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or attached to a polymer backbone through a linker group;
(ii) $R_{1a}$ and $R_{1d}$ are independently selected from the group consisting of alkyl, halogen substituted alkyl, alkenyl, alkynyl, aryl, hydroxyalkyl, aminoalkyl, alkyl group carrying a quaternary ammonium cation, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or attached to a polymer backbone through a linker group;
(iii) $R_{1e}$ and $R_{1g}$ are selected from the group consisting of hydrogen, alkyl, halogen substituted alkyl, alkenyl, alkynyl, aryl, hydroxyalkyl, aminoalkyl, alkyl group carrying a quaternary ammonium cation, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or are attached to a polymer backbone through a linker group, or part of a cyclic structure and joined by substituted or unsubstituted alkyl or heteroalkyl groups
(iv) $R_{1h}$ is selected from the group consisting of hydrogen, alkyl, halogen substituted alkyl, alkenyl, alkynyl, aryl, hydroxyalkyl, aminoalkyl, alkyl group carrying a quaternary ammonium cation, a heterocyclic moiety, thiol with a linker group, alkylsulfonate, alkylsulfate, carboxylalkyl, acrylamide or substituted acrylamides with a linker group, vinylsulfone with a linker group, sulfonyl ethyl sulfate with a linker group, halo-s-triazines with a linker group, halopyrimidines with a linker group, haloquinoxalines with a linker group, or attached to a polymer backbone through a linker group.

2. The compound according to claim 1, wherein $R_{1a}$ and $R_{1d}$ both are —$CH_2CH_2CH_2NH_2$; wherein $R_{1e}$ is propyl; and wherein $R_{1h}$ is hydrogen.

3. The compound according to claim 2, wherein the compound is attached to a polyethylene amine backbone through $R_{1a}$, $R_{1d}$, or $R_{1g}$.

4. The compound according to claim 2, wherein the compound is attached to a polyallylamine backbone through $R_{1a}$, $R_{1d}$, or $R_{1g}$.

5. The compound according to claim 2, wherein the compound is attached to a peptide or protein backbone through $R_{1a}$, $R_{1d}$, or $R_{1g}$.

6. The compound according to claim 1, wherein $R_{1a}$ is —$CH_2CH_2CH_2NH_2$; $R_{1d}$ is hexyl; $R_{1e}$ and $R_{1g}$ are part of a 6-membered ring; and $R_{1h}$ is hydrogen.

7. The compound according to claim 6, wherein the compound is attached to a polyethyleneimine backbone through $R_{1a}$ or $R_{1d}$.

8. The compound according to claim 6, wherein the compound is attached to a polyallylamine backbone through $R_{1a}$ or $R_{1d}$.

9. The compound according to claim 6, wherein the compound is attached to a peptide or protein backbone through $R_{1a}$ or $R_{1d}$.

10. The compound according to claim 1 wherein $R_{1a}$ and $R_{1d}$ both are —$CH_2CH_2CH_2NH_2$; $R_{1e}$ and $R_{1g}$ are part of a 6-membered ring; and $R_{1h}$ is hydrogen.

11. The compound according to claim 10, wherein the compound is attached to a polyethyleneimine backbone through $R_{1a}$ or $R_{1d}$.

12. The compound according to claim 10, wherein the compound is attached to a polyallylamine backbone through $R_{1a}$ or $R_{1d}$.

13. The compound according to claim 10, wherein the compound is attached to a peptide or protein backbone through $R_{1a}$ or $R_{1d}$.

14. The compound according to claim 1 wherein $R_{1a}$, $R_{1d}$, and $R_{1g}$ are all —$CH_2CH_2CH_2NH_2$, and wherein $R_{1h}$ is hydrogen.

15. The compound according to claim 14, wherein the compound is attached to a polyethyleneimine backbone through $R_{1a}$, $R_{1d}$, or $R_{1g}$.

16. The compound according to claim 14, wherein the compound is attached to a polyallylamine backbone through $R_{1a}$, $R_{1d}$, or $R_{1g}$.

17. The compound according to claim 1 wherein $R_{1a}$ and $R_{1d}$ both are —$CH_2CH_2CH_2NH_2$ and $R_{1e}$ is hexyl, and $R_{1h}$ is hydrogen.

18. The compound according to claim 16, wherein the compound is attached to a polyethylene amine backbone through $R_{1a}$ or $R_{1d}$.

19. The compound according to claim 16, wherein the compound is attached to a polyallylamine backbone through $R_{1a}$ or $R_{1d}$.

20. The compound according to claim 16, wherein the compound is attached to a peptide or protein backbone through $R_{1a}$ or $R_{1d}$.

\* \* \* \* \*